United States Patent [19]

Bird

[11] Patent Number: 5,484,805

[45] Date of Patent: Jan. 16, 1996

[54] HETEROCYCLENE DERIVATIVES

[75] Inventor: Thomas G. C. Bird, Witry-Les-Reims, France

[73] Assignees: Imperial Chemical Industries PLC, London, England; ICI Pharma, Cergy Cedex, France

[21] Appl. No.: 271,912

[22] Filed: Jul. 8, 1994

Related U.S. Application Data

[62] Division of Ser. No. 26,019, Mar. 4, 1993, Pat. No. 5,359,063, which is a division of Ser. No. 717,505, Jun. 19, 1991, Pat. No. 5,217,978.

[30] Foreign Application Priority Data

Jun. 21, 1990 [FR] France ................................ 90 401758
Jan. 15, 1991 [FR] France ................................ 91 400077

[51] Int. Cl.$^6$ ..................... A61K 31/40; C07D 207/36; C07D 207/42
[52] U.S. Cl. .................... 514/422; 514/431; 514/432; 514/444; 514/450; 514/451; 514/461; 548/527; 548/517; 549/9; 549/28; 549/59; 549/60; 549/346; 549/416; 549/472
[58] Field of Search .................... 548/527, 517; 549/9, 28, 59, 60, 346, 416, 472; 514/312, 422, 431, 432, 444, 450, 451, 461

[56] References Cited

U.S. PATENT DOCUMENTS

| | | | |
|---|---|---|---|
| 3,661,917 | 5/1972 | Kaiser et al. | 546/232 |
| 3,743,737 | 7/1973 | Kaiser et al. | 514/331 |
| 4,567,184 | 1/1986 | Musser et al. | 514/277 |
| 4,625,034 | 11/1986 | Neiss et al. | 546/152 |
| 4,631,287 | 12/1986 | Chakraborty et al. | 514/307 |
| 4,725,619 | 2/1988 | Chakraborty et al. | 514/442 |
| 4,728,668 | 3/1988 | Chakraborty et al. | 514/464 |
| 4,738,920 | 4/1988 | Uchida et al. | 435/6 |
| 4,794,188 | 12/1988 | Musser et al. | 546/152 |
| 4,839,369 | 6/1989 | Youssefyeh et al. | 514/314 |
| 4,876,346 | 10/1989 | Musser et al. | 546/172 |
| 4,918,081 | 4/1990 | Huang et al. | 514/311 |
| 4,920,130 | 4/1990 | Huang et al. | 514/314 |
| 4,920,131 | 4/1990 | Huang et al. | 514/311 |
| 4,920,132 | 4/1990 | Huang et al. | 514/314 |
| 4,920,133 | 4/1990 | Huang et al. | 514/314 |
| 4,921,862 | 5/1990 | Walker et al. | 514/312 |
| 5,141,551 | 8/1992 | Kawaguchi | 544/105 |
| 5,202,326 | 4/1993 | Crawley et al. | 514/255 |
| 5,208,259 | 5/1993 | Bird et al. | 514/460 |
| 5,217,969 | 6/1993 | Bruneau | 514/230.5 |
| 5,217,978 | 6/1993 | Bird | 514/312 |
| 5,240,941 | 8/1993 | Bruneau | 514/312 |

FOREIGN PATENT DOCUMENTS

| | | |
|---|---|---|
| 0110405 | 6/1984 | European Pat. Off. |
| 0181568 | 5/1986 | European Pat. Off. |
| 0190722 | 8/1986 | European Pat. Off. |
| 0200101 | 12/1986 | European Pat. Off. |
| 0271287 | 6/1988 | European Pat. Off. |
| 0349062 | 6/1989 | European Pat. Off. |

*Primary Examiner*—C. Warren Ivy
*Assistant Examiner*—D. Margaret M. Mach
*Attorney, Agent, or Firm*—Cushman Darby & Cushman

[57] ABSTRACT

The invention concerns a heterocyclene derivative of the formula I

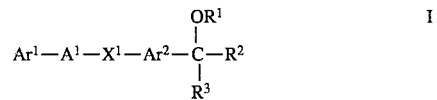

wherein

Ar$^1$ is optionally substituted phenyl, naphthyl or a 9- or 10-membered bicyclic heterocyclic moiety;

A$^1$ is a direct link to X$^1$ or (1–3C)alkylene;

X$^1$ is oxy, thio, sulphinyl, sulphonyl or imino;

Ar$^2$ is optionally substituted 5-membered heterocyclene moiety;

R$^1$ is (1–4C)alkyl, (3–4C)alkenyl or (3–4C)alkynyl; and

R$^2$ and R$^3$ together form a group of the formula —A$^2$—X$_2$—A$^3$— which, together with the carbon atom to which A$^2$ and A$^3$ are attached, defines a ring having 5 to 7 ring atoms, wherein each of A$^2$ and A$^3$ is (1–3C)alkylene and X$^2$ is oxy, thio, sulphinyl or sulphonyl;

or a pharmaceutically-acceptable salt thereof.

The compounds of the invention are inhibitors of the enzyme 5-lipoxygenase.

6 Claims, No Drawings

HETEROCYCLENE DERIVATIVES

This is a division of Application Ser. No. 08/026,019, filed Mar. 4, 1993 now U.S. Pat. No. 5,359,063, which in turn is a divisional of Application Ser. No. 07/717,505 filed Jun. 19, 1991, now U.S. Pat. No. 5,217,978.

This invention concerns novel heterocyclene derivatives and more particularly novel heterocyclene derivatives which are inhibitors of the enzyme 5-lipoxygenase (hereinafter referred to as 5-LO). The invention also concerns processes for the manufacture of said heterocyclene derivatives and novel pharmaceutical compositions containing them. Also included in the invention is the use of said heterocyclene derivatives in the treatment of various inflammatory and/or allergic diseases in which the direct or indirect products of 5-LO catalysed oxidation of arachidonic acid are involved, and the production of new medicaments for such use.

As stated above the heterocyclene derivatives described hereinafter are inhibitors of 5-LO, which enzyme is known to be involved in catalysing the oxidation of arachidonic acid to give rise via a cascade process to the physiologically active leukotrienes such as leukotriene $B_4$ ($LTB_4$) and the peptido-lipid leukotrienes such as leukotriene $C_4$ ($LTC_4$) and leukotriene $D_4$ ($LTD_4$) and various metabolites.

The biosynthetic relationship and physiological properties of the leukotrienes are summarised by G. W. Taylor and S. R. Clarke in *Trends in Pharmacological Sciences*, 1986, 7, 100–103. The leukotrienes and their metabolites have been implicated in the production and development of various inflammatory and allergic diseases such as inflammation of the joints (especially rheumatoid arthritis, osteoarthritis and gout), inflammation of the gastrointestinal tract (especially inflammatory bowel disease, ulcerative colitis and gastritis), skin disease (especially psoriasis, eczema and dermatitis) and respiratory disease (especially asthma, bronchitis and allergic rhinitis), and in the production and development of various cardiovascular and cerebrovascular disorders such as myocardial infarction, angina and peripheral vascular disease. In addition the leukotrienes are mediators of inflammatory diseases by virtue of their ability to modulate lymphocyte and leukocyte function. Other physiologically active metabolites of arachidonic acid, such as the prostaglandins and thromboxanes, arise via the action of the enzyme cyclooxygenase on arachidonic acid.

We have now discovered that certain heterocyclene derivatives are effective as inhibitors of the enzyme 5-LO and thus of leukotriene biosyntheses. Thus, such compounds are of value as therapeutic agents in the treatment of, for example, allergic conditions, psoriasis, asthma, cardiovascular and cerebrovascular disorders, and/or inflammatory and arthritic conditions, mediated alone or in part by one or more leukotrienes.

According to the invention there is provided a heterocyclene derivative of the formula I (set out hereinafter)

wherein $Ar^1$ is phenyl or naphthyl, or a 9- or 10-membered bicyclic heterocyclic moiety containing one or two nitrogen heteroatoms and optionally containing a further heteroatom selected from nitrogen, oxygen and sulphur, and $Ar^1$ may optionally bear up to five substituents selected from amino, halogeno, hydroxy, cyano, oxo, thioxo, (1–4C)alkyl, (1–4C)alkoxy, (1–4C)alkylthio, (1–4C)alkylsulphinyl, (1–4C)alkylsulphonyl, (1–4C)alkylamino, di-[(1–4C)alkyl]amino, (2–4C)alkanoyl, fluoro-(1–4C)alkyl, cyano-(1–4C)alkyl, phenyl, benzoyl and phenyl-(1–4C)alkyl, and wherein said phenyl, benzoyl or phenyl-(1–4C)alkyl substituents may optionally bear a substituent selected from halogeno, (1–4C)alkyl and (1–4C)alkoxy;

wherein $A^1$ is a direct link to $X^1$ or is (1–3C)alkylene;

wherein $X^1$ is oxy, thio, sulphinyl, sulphonyl or imino;

$Ar^2$ is a 5-membered heterocyclene moiety containing one heteroatom selected from nitrogen, oxygen and sulphur, which may optionally bear one substituent selected from halogeno, (1–4C)alkyl and (1–4C)alkoxy;

wherein $R^1$ is (1–4C)alkyl, (3–4C)alkenyl or (3–4C)alkynyl; and wherein $R^2$ and $R^3$ together form a group of the formula —$A^2$—$X^2$—$A^3$— which, together with the carbon atom to which $A^2$ and $A^3$ are attached, defines a ring having 5 to 7 ring atoms, wherein $A^2$ and $A^3$, which may be the same or different, each is (1–3C)alkylene and $X^2$ is oxy, thio, sulphinyl or sulphonyl, and which ring may bear one, two or three substituents, which may be the same or different, selected from hydroxy, (1–4C)alkyl and (1–4C)alkoxy;

or wherein $R^1$ and $R^2$ together form a group of the formula —$A^2$—$X^2$—$A^3$— which, together with the oxygen atom to which $A^2$ is attached and with the carbon atom to which $A^3$ is attached, defines a ring having 5 to 7 ring atoms, wherein $A^2$ and $A^3$, which may be the same or different, each is (1–3C)alkylene and $X^2$ is oxy, thio, sulphinyl or sulphonyl, and which ring may bear one, two or three (1–4C)alkyl substituents, and wherein $R^3$ is (1–4C)alkyl, (2–4C)alkenyl or (2–4C)alkynyl;

or a pharmaceutically-acceptable salt thereof.

According to a further aspect of the invention there is provided a heterocyclene derivative of the formula I as defined immediately above wherein further optional substituents on $Ar^1$ include α,α-difluorobenzyl, α-hydroxybenzyl and α-[(1–4C)alkoxy]benzyl, which substituents may optionally bear a substituent selected from halogeno, (1–4C)alkyl and (1–4C)alkoxy.

According to a further aspect of the invention there is provided a heterocyclene derivative of the formula I wherein $Ar^1$ is phenyl or naphthyl, or a 9- or 10-membered bicyclic heterocyclic moiety containing one or two nitrogen heteroatoms and optionally containing a further heteroatom selected from nitrogen, oxygen and sulphur, and $Ar^1$ may optionally bear up to five substituents selected from amino, halogeno, hydroxy, cyano, oxo, thioxo, (1–4C)alkyl, (1–4C)alkoxy, (1–4C)alkylthio, (1–4C)alkylsulphinyl, (1–4C)alkylsulphonyl, (1–4C)alkylamino, di-[(1–4C)alkyl]amino, (2–4C)alkanoyl, fluoro-(1–4C)alkyl, cyano-(1–4C)alkyl, phenyl, benzoyl, phenyl-(1–4C)alkyl, α,α-difluorobenzyl, α-hydroxybenzyl and α-[(1–4C)alkoxy]benzyl, and wherein said six last-mentioned substituents may optionally bear up to five substituents selected from halogeno, trifluoromethyl, (1–4C)alkyl and (1–4C)alkoxy;

wherein $A^1$ is a direct link to $X^1$ or is (1–3C)alkylene;

wherein $X^1$ is oxy, thio, sulphinyl, sulphonyl or imino;

$Ar^2$ is a 5-membered heterocyclene moiety containing one heteroatom selected from nitrogen, oxygen and sulphur, which may optionally bear one substituent selected from halogeno, (1–4C)alkyl and (1–4C)alkoxy;

wherein $R^1$ is (1–4C)alkyl, (3–4C)alkenyl or (3–4C)alkynyl; and wherein $R^2$ and $R^3$ together form a group of the formula $-A^2-X^2-A^3-$ which, together with the carbon atom to which $A^2$ and $A^3$ are attached, defines a ring having 5 to 7 ring atoms, wherein $A^2$ and $A^3$, which may be the same or different, each is (1–3C)alkylene and $X^2$ is oxy, thio, sulphinyl or sulphonyl, and which ring may bear one, two or three substituents, which may be the same or different, selected from hydroxy, (1–4C)alkyl and (1–4C)alkoxy;

or wherein $R^1$ and $R^2$ together form a group of the formula $-A^2-X^2-A^3-$ which, together with the oxygen atom to which $A^2$ is attached and with the carbon atom to which $A^3$ is attached, defines a ring having 5 to 7 ring atoms, wherein $A^2$ and $A^3$, which may be the same or different, each is (1–3C)alkylene and $X^2$ is oxy, thio, sulphinyl or sulphonyl, and which ring may bear one, two or three (1–4C)alkyl substituents, and wherein $R^3$ is (1–4C)alkyl, (2–4C)alkenyl or (2–4C)alkynyl;

or a pharmaceutically-acceptable salt thereof.

The chemical formulae referred to herein by Roman numerals are set out for convenience on a separate sheet hereinafter.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of the formula I defined above may exhibit the phenomenon of tautomerism and any formula drawing presented herein may represent only one of the possible tautomeric forms, the invention includes in its definition any tautomeric form of a compound of the formula I which possesses the property of inhibiting 5-LO and is not to be limited merely to any one tautomeric form utilised within the formulae drawings.

It is further to be understood that, insofar as certain of the compounds of formula I defined above may exist in optically active or racemic forms by virtue of one or more substituents containing an asymmetric carbon atom, the invention includes in its definition any such optically active or racemic form which possesses the property of inhibiting 5-LO. The synthesis of optically active forms may be carried out by standard techniques of organic chemistry well known in the art, for example by synthesis from optically active starting materials or by resolution of a racemic form. Similarly, inhibitory properties against 5-LO may be evaluated using the standard laboratory techniques referred to hereinafter.

Suitable values for the generic terms referred to above include those set out below.

A suitable value for $Ar^1$ when it is a 9- or 10-membered bicyclic heterocyclic moiety containing one or two nitrogen heteroatoms and optionally containing a further heteroatom selected from nitrogen, oxygen and sulphur is, for example, a 9- or 10-membered benzo-fused heterocyclic moiety-such as indolyl, isoindolyl, benzimidazolyl, 1H-indazolyl, benzoxazolyl, benzothiazolyl, quinolyl, isoquinolyl, cinnolinyl, quinazolinyl, quinoxalinyl, 4H-1,4-benzoxazinyl or 4H-1,4-benzothiazinyl, or a hydrogenated derivative thereof such as indolinyl, 2,3-dihydrobenzimidazolyl, 2,3-di. hydrobenzoxazolyl, 2,3-dihydrobenzothiazolyl, 1,2-dihydroquinolyl, 1,2,3,4-tetrahydroquinolyl, 1,2-dihydroisoquinolyl, 2,3-dihydro-4H-1,4-benzoxazinyl or 2,3-dihydro-4H-1,4-benzothiazinyl; or, for example, a 9- or 10-membered pyrido-fused heterocyclic moeity such as 1H-pyrrolo[2,3-b]pyridyl, imidazo[4,5-b]pyridyl, 1,7-naphthyridinyl, 1,8-naphthyridinyl, pyrido[2,3-d]pyrimidinyl, pyrido[2,3-b]pyrazinyl, 4H-pyrido[3,2-b][1,4]oxazinyl and 4H-pyrido[3,2-b][1,4]thiazinyl, or a hydrogenated derivative thereof.

The heterocyclic moiety may be attached through any available position including from either of the two rings of the bicyclic heterocyclic moiety and including through an available nitrogen atom. The heterocyclic moiety may bear a suitable substituent such as, for example, a (1–4C)alkyl, phenyl, benzoyl or phenyl-(1–4C)alkyl substituent on an available nitrogen atom.

Suitable values for substituents which may be present on $Ar^1$ or $Ar^2$, or on a phenyl, benzoyl, phenyl-(1–4C)alkyl, $\alpha,\alpha$-difluorobenzyl, $\alpha$-hydroxybenzyl or $\alpha$-[(1–4C)alkoxy]benzyl substituent on $Ar^1$, include, for example:

for halogeno: fluoro, chloro, bromo and iodo;

for (1–4C)alkyl: methyl, ethyl, propyl, isopropyl, butyl, isobutyl, sec-butyl and tert-butyl;

for (1–4C)alkoxy: methoxy, ethoxy, propoxy, isopropoxy and butoxy.

Suitable values for substituents which may be present on $Ar^1$ include, for example:

for fluoro-(1–4C)alkyl: fluoromethyl, difluoromethyl, trifluoromethyl, 2-fluoroethyl, 2,2,2-trifluoroethyl and pentafluoroethyl;

for (1–4C)alkylamino: methylamino, ethylamino, propylamino and butylamino;

for di-[(1–4C)alkyl]amino: dimethylamino, diethylamino and dipropylamino;

for (1–4C)alkythio: methylthio, ethylthio, propylthio, isopropylthio and butylthio;

for (1–4C)alkylsulphinyl: methylsulphinyl, ethylsulphinyl, propylsulphinyl, isopropylsulphinyl and butylsulphinyl;

for (1–4C)alkylsulphonyl: methylsulphonyl, ethylsulphonyl, propylsulphonyl, isopropylsulphonyl and butylsulphonyl;

for (2–4C)alkanoyl: acetyl, propionyl and butyryl;

for cyano-(1–4C)alkyl: cyanomethyl, 1-cyanoethyl, 2-cyanoethyl, 3-cyanopropyl and 2-cyanoprop-2-yl;

for phenyl-(1–4C)alkyl: benzyl, phenethyl, 3-phenylpropyl and $\alpha$-methylbenzyl.

for $\alpha$-[(1–4C)alkoxy]benzyl: $\alpha$-methoxybenzyl and $\alpha$-ethoxybenzyl.

A suitable value for $A^1$ when it is (1–3C)alkylene is, for example, methylene, ethylene or trimethylene.

A suitable value for $Ar^2$ when it is a 5-membered heterocyclene moiety containing one heteroatom selected from nitrogen oxygen and sulphur is, for example, pyrrolylene, furylene or thienylene. Conveniently $Ar^2$ is 2,4- or 2,5-pyrrolylene, 2,4- or 2,5-furylene or 2,4- or 2,5-thienylene. It is to be understood in the case of the 2,4-heterocyclene derivatives defined hereinbefore that $X^1$ may be attached to either the 2-position or the 4-position.

A suitable value for $R^1$ when it is (1–4C)alkyl is, for example, methyl, ethyl, propyl or butyl; when it is (3–4C)alkenyl is, for example, allyl, 2-butenyl or 3-butenyl; and when it is (3–4C)alkynyl is, for example, 2-propynyl or 2-butynyl.

When $R^2$ and $R^3$ together form a group of the formula $-A^2-X^2-A^3-$, which, together with the carbon atom to which $A^2$ and $A^3$ are attached, defines a ring having 5 to 7 ring atoms then a suitable value for $A^2$ or $A^3$, which may be the same or different, when each is (1–3C)alkylene is, for example, methylene, ethylene or trimethylene. Suitable values for the substituents which may be present on said 5- to 7-membered ring include for example:

for (1–4C)alkyl: methyl, ethyl, propyl, isopropyl, butyl and isobutyl;

for (1–4C)alkoxy: methoxy, ethoxy, propoxy, isopropoxy and butoxy.

When $R^1$ and $R^2$ together form a group of the formula —$A^2$—$X^2$—$A^3$— which together with the oxygen atom to which $A^2$ is attached and with the carbon atom to which $A^3$ is attached, defines a ring having 5 to 7 ring atoms then a suitable value for $A^2$ or $A^3$, which may be the same or different, when each is (1–3C)alkylene is, for example, methylene, ethylene or trimethylene. Suitable values for the (1–4C)alkyl substituents which may be present on said 5- to 7-membered ring include, for example, methyl, ethyl, propyl, isopropyl and butyl.

A suitable value for $R^3$ when it is (1–4C)alkyl is, for example, methyl, ethyl, propyl or butyl; when it is (2–4C)alkenyl is, for example, vinyl, allyl, 2-butenyl or 3-butenyl; and when it is (2–4C)alkynyl is, for example, ethynyl, 2-propynyl or 2-butynyl.

A suitable pharmaceutically-acceptable salt of a novel compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a novel compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Particular novel compounds of the invention are, for example, heterocyclene derivatives of the formula I wherein:

(a) $Ar^1$ is phenyl or naphthyl which may optionally bear one, two or three substituents selected from any of those substituents on $Ar^1$ defined hereinbefore other than oxo and thioxo;

(b) $Ar^1$ is phenyl or naphth-2-yl which may optionally bear one or two substituents selected from fluoro, chloro, methyl, ethyl, isopropyl, tert-butyl, methoxy, trifluoromethyl, 2-cyanoprop-2-yl, phenyl and benzoyl, and wherein said phenyl or benzoyl substituents may optionally bear a substituent selected from chloro, methyl and methoxy; and $A^1$, $X^1$, $Ar^2$, $R^1$, $R^2$ and $R^3$ have any of the meanings defined hereinbefore;

(c) $Ar^1$ is phenyl or naphth-2-yl which may optionally bear one or two substituents selected from fluoro, chloro, methyl, ethyl, isopropyl, tert-butyl, methoxy, trifluoromethyl, 2-cyanoprop-2-yl, phenyl, benzoyl, benzyl, α,α-difluorobenzyl and α-methoxybenzyl, and wherein said phenyl, benzoyl, benzyl, α,α-difluorobenzyl or α-methoxybenzyl substituents may optionally bear a substituent selected from fluoro, chloro, methyl and methoxy; and $A^1$, $X^1$, $Ar^3$, $R^1$, $R^2$ and $R^3$ have any of the meanings defined hereinbefore;

(d) $Ar^1$ is phenyl or naphth-2-yl which may optionally bear one or two substituents selected from fluoro, chloro, bromo, methyl, ethyl, isopropyl, tert-butyl, methoxy, trifluoromethyl, 2-cyanoprop-2-yl, phenyl, benzoyl, benzyl, α,α-difluorobenzyl, α-hydroxybenzyl and α-methoxybenzyl, and wherein said six last-mentioned substituents may optionally bear up to five substituents selected from fluoro, chloro, trifluoromethyl, methyl and methoxy; and $A^1$, $X^1$, $Ar^2$, $R^1$, $R^2$ and $R^3$ have any of the meanings defined hereinbefore;

(e) $Ar^1$ is a 9- or 10-membered benzo-fused heterocyclic moiety containing one or two nitrogen heteroatoms and optionally containing a further heteroatom selected from oxygen and sulphur, which heterocyclic moiety may optionally bear one or two oxo or thioxo substituents and up to three further substituents selected from any of those substituents on $Ar^1$ defined hereinbefore other than oxo or thioxo;

and $A^1$, $X^1$, $Ar^2$, $R^1$, $R^2$ and $R^3$ have any of the meanings defined hereinbefore;

(f) $Ar^1$ is indolyl, indolinyl, benzimidazolyl, 2,3-dihydrobenzimidazolyl, benzoxazolyl, 2,3-dihydrobenzoxazolyl, benzothiazolyl, 2,3-dihydrobenzothiazolyl, quinolyl, 1,2-dihydroquinolyl, isoquinolyl, 1,2-dihydroisoquinolyl, quinoxalinyl, 2,3-dihydro-4H-1,4-benzoxazinyl or 2,3-dihydro-4H-1,4-benzothiazinyl, which may optionally bear one or two oxo or thioxo substituents and up to three further substituents selected from any of those substituents on $Ar^1$ defined hereinbefore other than oxo or thioxo; and $A^1$, $X^1$, $Ar^2$, $R^1$, $R^2$ and $R^3$ have any of the meanings defined hereinbefore;

(g) $Ar^1$ is quinolyl, 1,2-dihydroquinolyl, 1,2,3,4-tetrahydroquinolyl or 2,3-dihydro-4H-1,4-benzoxazinyl which may optionally bear one oxo or thioxo substituent and up to three further substituents selected from any of those substituents on $Ar^1$ defined hereinbefore other than oxo or thioxo; and $A^1$, $X^1$, $Ar^2$, $R^1$, $R^2$ and $R^3$ have any of the meanings defined hereinbefore;

(h) $Ar^1$ is 2-indolyl, 3-indolyl, 5-indolyl, 6-indolyl, 2-benzimidazolyl, 5-benzimidazolyl, 6-benzimidazolyl, 2-benzoxazolyl, 5-benzoxazolyl, 6-benzoxazolyl, 2-benzothiazolyl, 5-benzothiazolyl, 6-benzothiazolyl, 2-quinolyl, 3-quinolyl, 6-quinolyl, 7-quinolyl, 3-isoquinolyl, 6-isoquinolyl, 7-isoquinolyl, 2-quinoxalinyl, 6-quinoxalinyl, 4H-1,4-benzoxazin-6-yl or 4H-1,4-benzothiazin-6-yl, which may optionally bear one or two substituents selected from any of those substituents on $Ar^1$ defined hereinbefore other than oxo or thioxo; and $A^1$, $X^1$, $Ar^2$, $R^1$, $R^2$ and $R^3$ have any of the meanings defined hereinbefore;

(i) $Ar^1$ is 2-oxoindolinyl, 2,3-dioxoindolinyl, 2-oxo-2,3-dihydrobenzimidazolyl, 2-oxo-2,3-dihydrobenzoxazolyl, 2-oxo-2,3-dihydrobenzothiazolyl, 2-oxo-1,2-dihydroquinolinyl, 3-oxo-2,3-dihydro-4H-1,4-benzoxazinyl or 3-oxo-2,3-dihydro-4H- 1,4-benzothiazinyl, or the corresponding thioxo derivatives thereof, which may optionally bear up to three substituents selected from any of those substituents on $Ar^1$ defined hereinbefore other than oxo or thioxo; and $A^1$, $X^1$, $Ar^2$, $R^1$, $R^2$ and $R^3$ have any of the meanings defined hereinbefore;

(j) $Ar^1$ is 2-oxo-1,2-dihydroquinolinyl, 2-thioxo-1,2-dihydroquinolinyl, 2-oxo-1,2,3,4-tetrahydroquinolinyl, 2-thioxo-1,2,3,4-tetrahydroquinolinyl or 3-oxo-2,3-dihydro-4H 1,4-benzoxazinyl which may optionally bear up to three substituents selected from any of those substituents on $Ar^1$defined hereinbefore other than oxo or thioxo; and $A^1$, $X^1$, $Ar^2$, $R^1$, $R^2$ and $R^3$have any of the meanings defined hereinbefore;

(k) $Ar^1$ is 2-oxoindolin-5-yl, 2,3-dioxoindolin-5-yl, 2-oxo-2,3-dihydrobenzimidazol- 5-yl, 2-oxo-2,3-dihydrobenzoxazol-5-yl, 2-oxo-2,3-dihydrobenzothiazol-5-yl, 2-oxo-1,2-dihydroquinolin-3-yl, 2-oxo-1,2-dihydroquinolin-6-yl, 2-oxo-1,2-dihydroquinolin-7-yl, 3-oxo-2,3-dihydro-4H-1,4-benzoxazin-7-yl or 3-oxo-2,3-dihydro-4H- 1,4-benzothiazol-7-yl, which may optionally bear up to three substituents selected from any of those substituents on $Ar^1$ defined hereinbefore other than oxo or thioxo; and $A^1$, $X^1$, $Ar^2$, $R^1$, $R^2$ and $R^3$ have any of the meanings defined hereinbefore;

(l) $A^1$ is a direct link to $X^1$, and $X^1$ is oxy thio sulphinyl or sulphonyl; and $Ar^1$, $Ar^2$, $R^1$, $R^2$ and $R^3$ have any of the meanings defined hereinbefore;

(m) $A^1$ is methylene and $X^1$ is oxy, thio, sulphinyl or sulphonyl; and $Ar^1$, $Ar^2$, $R^1$, $R^2$ and $R^3$ have any of the meanings defined hereinbefore;

(n) $Ar^2$ is 2,4- or 2,5-furylene or 2,4- or 2,5-thienylene, which may optionally bear a substituent selected from methyl, fluoro, chloro and methoxy; and $Ar^1$, $A^1$, $X^1$, $R^1$, $R^2$ and $R^3$ have any of the meanings defined hereinbefore;

(o) $Ar^2$ is 2,4- or 2,5-furylene or 2,4- or 2,5-thienylene, which may optionally bear a substituent selected from methyl, fluoro, chloro, bromo and methoxy; and $Ar^1$, $A^1$, $X^1$, $R^1$, $R^2$ and $R^3$ have any of the meanings defined hereinbefore;

(p) $R^1$ is methyl, ethyl, allyl or 2-propynyl; and $Ar^1$, $A^1$, $X^1$, $Ar^2$, $R^2$ and $R^3$ have any of the meanings defined hereinbefore;

(q) $R^2$ and $R^3$ together form a group of the formula —$A^2$—$X^2$—$A^3$— which, together with the carbon atom to which $A^2$ and $A^3$ are attached, defines a ring having 5 to 7 ring atoms, wherein $A^2$ and $A^3$, which may be the same or different, each is methylene, ethylene or trimethylene and $X^2$ is oxy, and which ring may bear one or two substituents selected from hydroxy, methyl, ethyl, propyl, methoxy and ethoxy; and $Ar^1$, $A^1$, $X^1$, $Ar^2$ and $R^1$ have any of the meanings defined hereinbefore; or (r) $R^1$ and $R^2$ together form a group of the formula —$A^2$—$X^2$—$A^3$— which, together with the oxygen atom to which $A^2$ is attached and with the carbon atom to which $A^3$ is attached, defines a ring having 5 to 7 ring atoms, wherein $A^2$ and $A^3$, which may be the same or different, each is methylene or ethylene and $X^2$ is oxy, and which ring may bear one, two or three substituents selected from methyl, ethyl and propyl, and $R^3$ is methyl or ethyl; and $Ar^1$, $A^1$, $X^1$ and $Ar^2$ have any of the meanings defined hereinbefore;
or a pharmaceutically-acceptable salt thereof.

A preferred compound of the invention comprises a heterocyclene derivative of the formula I
wherein $Ar^1$ is phenyl or naphth-2-yl which may optionally bear one or two substituents selected from fluoro, chloro, methyl, ethyl, isopropyl, tert-butyl, methoxy, trifluoromethyl, 2-cyanoprop-2-yl, phenyl and benzoyl and wherein said phenyl or benzoyl substituents may optionally bear a substituent selected from chloro, methyl and methoxy;

$A^1$ is a direct link to $X^1$, or is methylene;

$X^1$ is oxy, thio, sulphinyl or sulphonyl;

$Ar^2$ is 2,4- or 2,5-furylene or 2,4- or 2,5-thienylene;

$R^1$ is methyl, ethyl, allyl or 2-propynyl; and $R^2$ and $R^3$ together form a group of the formula —$A^2$—$X^2$—$A^3$— which, together with the carbon atom to which $A^2$ and $A^3$ are attached, defines a ring having 5 or 6 ring atoms, wherein $A^2$ is ethylene, $A^3$ is methylene or ethylene, and $X^2$ is oxy, and which ring may bear one or two substituents selected from methyl and ethyl;

or $R^1$ and $R^2$ together form a group of the formula —$A^2$—$X^2$—$A^3$— which, together with the oxygen atom to which $A^2$ is attached and with the carbon atom to which $A^3$ is attached, defines a ring having 5 ring atoms, wherein $A^2$ is methylene, $A^3$ is methylene, and $X^2$ is oxy, and which ring may bear one, two or three substituents selected from methyl and ethyl, and $R^3$ is methyl or ethyl;
or a pharmaceutically-acceptable salt thereof.

A further preferred compound of the invention comprises a heterocyclene derivative of the formula I wherein
$Ar^1$ is 2-oxoindolin-5-yl, 2,3-dioxoindolin-5-yl, 2-oxo-2,3-dihydrobenzimidazol-5-yl, 2-oxo-2,3-dihydrobenzoxazol-5-yl, 2-oxo-2,3-dihydrobenzothiazol-5-yl, 2-oxo-1,2-dihydroquinolin-3-yl, 2-oxo- 1,2-dihydroquinolin-6-yl, 2-oxo-1,2-dihydroquinolin-7-yl, 3-oxo-2,3-dihydro-4H-1,4-benzoxazin-7-yl or 3-oxo-2,3-dihydro-4H-1,4-benzothiazol-7-yl, which may optionally bear one, two or three substituents selected from fluoro, chloro, methyl, ethyl, 2-fluoroethyl, phenyl and benzyl;

$A^1$ is a direct link to $X^1$, or is methylene;

$X^1$ is oxy, thio, sulphinyl or sulphonyl;

$Ar^2$ is 2,4- or 2,5-furylene or 2,4- or 2,5-thienylene;

$R^1$ is methyl, ethyl, allyl or 2-propynyl; and $R^2$ and $R^3$ together form a group of the formula —$A^2$—$X^2$—$A^3$— which, together with the carbon atom to which $A^2$ and $A^3$ are attached, defines a ring having 5 or 6 ring atoms, wherein $A^2$ is ethylene, $A^3$ is methylene or ethylene, and $X^2$ is oxy, and which ring may bear one or two substituents selected from methyl and ethyl;

or $R^1$ and $R^2$ together form a group of the formula —$A^2$—$X^2$—$A^3$— which, together with the oxygen atom to which $A^2$ is attached and with the carbon atom to which $A^3$ is attached, defines a ring having 5 ring atoms, wherein $A^2$ is methylene, $A^3$ is methylene, and $X^2$ is oxy, and which ring may bear one, two or three substituents selected from methyl and ethyl, and $R^3$ is methyl or ethyl;
or a pharmaceutically-acceptable salt thereof.

A further preferred compound of the invention comprises a heterocyclene derivative of the formula I wherein
$Ar^1$ phenyl which may optionally bear a substituent selected from fluoro, chloro, methyl, tert-butyl, phenyl and benzoyl, and wherein said phenyl or benzoyl substituent may optionally bear a chloro substituent, or $Ar^1$ is naphth-2-yl which may optionally bear a substituent selected from fluoro, chloro and methyl;

$A^1$ is a direct link to $X^1$, or is methylene;

$X^1$ is oxy, thio, sulphinyl or sulphonyl;

$Ar^2$ is 2,5-furylene or 2,5-thienylene;

$R^1$ is methyl, ethyl or allyl; and $R^2$ and $R^3$ together form a group of the formula —$A^2$—$X^2$—$A^3$— which, together with the carbon atom to which $A^2$ and $A^3$ are attached, defines a ring having 5 or 6 ring atoms, wherein $A^2$ is ethylene, $A^3$ is methylene or ethylene and $X^2$ is oxy, and which ring may bear a substituent selected from methyl and ethyl;
or a pharmaceutically-acceptable salt thereof.

A further preferred compound of the invention comprises a heterocyclene derivative of the formula I wherein
$Ar^1$ is phenyl which may optionally bear a substituent selected from fluoro, chloro, methyl, tert-butyl, phenyl, benzoyl, benzyl and α,α-difluorobenzyl and wherein said phenyl, benzoyl, benzyl or α,α-difluorobenzyl substituent may optionally bear a fluoro or chloro substituent, or $Ar^1$ is naphth-2-yl which may optionally bear a substituent selected from fluoro, chloro and methyl;

$A^1$ is a direct link to $X^1$, or is methylene;

$X^1$ is oxy, thio, sulphinyl or sulphonyl;

$Ar^2$ is 2,5-furylene or 2,5-thienylene;

$R^1$ is methyl, ethyl or allyl; and $R^2$ and $R^3$ together form a group of the formula —$A^2$—$X^2$—$A^3$— which, together with the carbon atom to which $A^2$ and $A^3$ are attached, defines a ring having 5 or 6 ring atoms, wherein $A^2$ is ethylene, $A^3$ is methylene or ethylene and $X^2$ is oxy, and which ring may bear a substituent selected from methyl and ethyl;

or a pharmaceutically-acceptable salt thereof.

A further preferred compound of the invention comprises a heterocyclene derivative of the formula I wherein $Ar^1$ is phenyl which may optionally bear a substituent selected from fluoro, chloro, methyl, tert-butyl, phenyl, benzoyl, benzyl, α,α-difluorobenzyl or α-hydroxybenzyl, and wherein said 5 last-mentioned substituents may optionally bear up to five substituents selected from fluoro, chloro and trifluoromethyl, or $Ar^1$ is naphth-2-yl which may optionally bear a substituent selected from fluoro, chloro and methyl;

$A^1$ is a direct link to $X^1$, or is methylene;

$X^1$ is oxy, thio, sulphinyl or sulphonyl;

$Ar^2$ is 2,5-furylene or 2,5-thienylene;

$R^1$ is methyl, ethyl or allyl; and $R^2$ and $R^3$ together form a group of the formula —$A^2$—$X^2$—$A^3$— which, together with the carbon atom to which $A^2$ and $A^3$ are attached, defines a ring having 5 or 6 atoms, wherein $A^2$ is ethylene, $A^3$ is methylene or ethylene and $X^2$ is oxy, and which ring may bear a substituent selected from methyl and ethyl;

or a pharmaceutically-acceptable salt thereof.

A further preferred compound of the invention comprises a heterocyclene derivative of the formula I wherein $Ar^1$ is 1,3,3-trimethyl-2-oxoindolin-5-yl, 1,3-dimethyl-2-oxo- 2,3-dihydrobenzimidazol-5-yl, 3-methyl-2-oxo-2, 3-dihydrobenzothiazol- 6-yl, 1-methyl-2-oxo-1,2-dihydroquinolin-6-yl, 1-ethyl-2-oxo-1,2 -dihydroquinolin-6-yl, 4-methyl-3-oxo-2,3-dihydro-4H-1,4-benzoxazin- 7yl or 2,2,4-trimethyl-3-oxo-2,3-dihydro-4H-1,4-benzoxazin-7-yl;

$A^1$ is a direct link to $X^1$, or is methylene;

$X^1$ is oxy, thio, sulphinyl or sulphonyl;

$Ar^2$ is 2,5-furylene or 2,5-thienylene;

$R^1$ is methyl, ethyl or allyl; and $R^2$ and $R^3$ together form a group of the formula —$A^2$—$X^2$—$A^3$— which, together with the carbon atom to which $A^2$ and $A^3$ are attached, defines a ring having 5 or 6 ring atoms, wherein $A^2$ is ethylene, $A^3$ is methylene or ethylene and $X^2$ is oxy, and which ring may bear a substituent selected from methyl and ethyl;

or a pharmaceutically-acceptable salt thereof.

A further preferred compound of the invention comprises a heterocyclene derivative of the formula I wherein $Ar^1$ is 1-methyl-2-oxo-1,2-dihydroquinolin-6-yl, 1-ethyl-2-oxo-1,2 -dihydroquinolin-6-yl, 1-methyl-2-oxo-1,2,3,4-tetrahydroquinolin-6-yl, 1-ethyl-2-oxo-1,2,3,4-tetrahydroquinolin-6-yl or the corresponding 2-thioxo derivatives, or $Ar^1$ is 4-methyl-3-oxo-2,3-dihydro-4H-1,4 -benzoxazin-7-yl;

$A^1$ is a direct link to $X^1$;

$X^1$ is oxy, thio, sulphinyl or sulphonyl;

$Ar^2$ is 2,5-thienylene;

$R^1$ is methyl, ethyl or allyl; and $R^2$ and $R^3$ together form a group of the formula —$A^2$—$X^2$—$A^3$— which, together with the carbon atom to which $A^2$ and $A^3$ are attached, defines a ring having 5 or 6 ring atoms, wherein $A^2$ is ethylene, $A^3$ is methylene or ethylene and $X^2$ is oxy, and which ring may bear a substituent selected from methyl and ethyl;

or a pharmaceutically-acceptable salt thereof.

An especially preferred compound of the invention comprises a heterocyclene derivative of the formula I wherein $Ar^1$ is 4-tert-butylphenyl or naphth-2-yl;

$A^1$ is a direct link to $X^1$;

$X^1$ is thio;

$Ar^2$ is 2,5-thienylene;

$R^1$ is methyl; and $R^2$ and $R^3$ together form a group of the formula —$A^2$—$X^2$—$A^3$— which, together with the carbon ,atom to which $A^2$ and $A^3$ are attached, defines a ring having 5 or 6 ring atoms, wherein $A^2$ is ethylene, $A^3$ is methylene or ethylene and $X^2$ is oxy, and which ring may bear a methyl substituent alpha to $X^2$;

or a pharmaceutically-acceptable salt thereof.

An especially preferred compound of the invention comprises a heterocyclene derivative of the formula I wherein $Ar^1$ is 1-methyl-2 -oxo-1,2-dihydroquinolin-6-yl, 1-methyl-2-thioxo-1,2-dihydroquinolin- 6-yl, 1-methyl-2-oxo-1,2,3,4-tetrahydroquinolin-6-yl, 1-methyl-2-thioxo-1,2,3,4-tetrahydroquinolin-6-yl or 4-methyl-3-oxo- 2,3-dihydro-4H-1,4-benzoxazin-7-yl;

$A^1$ is a direct link to $X^1$;

$X^1$ is thio;

$Ar^2$ is 2,5-thienylene;

$R^1$ is methyl; and $R^2$ and $R^3$ together form a group of the formula —$A^2$—$X^2$—$A^3$— which, together with the carbon atom to which $A^2$ and $A^3$ are attached, defines a ring having 6 ring atoms, wherein $A^2$ is ethylene, $A^3$ is ethylene and $X^2$ is oxy, and which ring may bear a methyl substituent alpha to $X^2$;

or a pharmaceutically-acceptable salt thereof.

A specific especially preferred compound of the invention is the following heterocyclene derivative of the formula I, or a pharmaceutically-acceptable salt thereof:

4-[5-(4-tert-butylphenylthio)thien-2-yl]-4-methoxytetrahydropyran.

A further specific especially preferred compound of the invention is any of the following heterocyclene derivatives of the formula I, or pharmaceutically-acceptable salts thereof:

4-methoxy-4-[5-(1-methyl-2-oxo-1,2,3,4-tetrahydroquinolin-6 -ylthio)thien-2-yl]tetrahydropyran, 4-methoxy-4-[5-(1-methyl-2-oxo-1,2-dihydroquinolin-6-ylthio)thien-2yl] tetrahydropyran, 4-methoxy-4-[5-(1-methyl-2-thioxo-1,2,3,4-tetrahydroquinolin-6 -ylthio)thien-2-yl]tetrahydropyran, 4-methoxy-4-[5-(4-methyl-3-oxo-2,3-dihydro-4H-1,4-benzoxazin-7 -ylthio)thien-2-yl]tetrahydropyran, (2S,4R)-4-methoxy-2-methyl-4-[5-(1-methyl-2-thioxo-1,2, 3,4 -tetrahydroquinolin-6-ylthio)thien-2-yl]tetrahydropyran.

A further specific especially preferred compound of the invention is the following heterocyclene derivative of the formula I, or a pharmaceutically-acceptable salt thereof:

4-[5-(4-(alpha-hydroxybenzyl)phenylthio)thien-2-yl]-4-methoxytetrahydropyran.

A compound of the invention comprising a heterocylene derivative of the formula I, or a pharmaceutically-acceptable salt thereof, may be prepared by any process known to be applicable to the preparation of structurally-related compounds. Such procedures are provided as a further feature of the invention and are illustrated by the following representative examples in which, unless otherwise stated, $Ar^1$, $A^1$, $X^1$, $Ar^2$, $R^1$, $R^2$ and $R^3$ have any of the meanings defined hereinbefore.

(a) The coupling, preferably in the presence of a suitable base, of a compound of the formula $Ar^1$—$A^1$—$X^1$—H with a compound of the formula II wherein Z is a displaceable group; provided that, when there is an amino, alkylamino or hydroxy group in $Ar^1$, $R^2$ or $R^3$, any amino, alkylamino or hydroxy group may be protected by a conventional protecting group or alternatively any such group need not be protected, whereafter any undesired protecting group in $Ar^1$, $R^2$ or $R^3$ is removed by conventional means.

A suitable displaceable group Z is, for example, a halogeno or sulphonyloxy group, for example a fluoro, chloro, bromo, iodo, methanesulphonyloxy or toluene-p-sulphonyloxy group.

A suitable base for the coupling reaction is, for example, an alkali or alkaline earth metal carbonate, (1–4C)alkoxide, hydroxide or hydride, for example sodium carbonate, potassium carbonate, sodium ethoxide, sodium butoxide, sodium hydroxide, potassium hydroxide, sodium hydride or potassium hydride; or an organometallic base such as (1–4C)alkyl-lithium, for example n-butyl-lithium. The coupling reaction is conveniently performed in a suitable inert solvent or diluent, for example N,N-dimethylformamide, N,N-dimethylacetamide, N-methylpyrrolidin-2-one, dimethylsulphoxide, acetone, 1,2-dimethoxyethane or tetrahydrofuran, and at a temperature in the range, for example, 10° to 150° C., conveniently at or near 100° C.

Conveniently the reaction may be performed in the presence of a suitable catalyst, for example a metallic catalyst, for example palladium(O) or copper(I) such as tetrakis(triphenylphosphine)palladium, cuprous chloride or cuprous bromide.

A suitable protecting group for an amino or alkylamino group is, for example, an acyl group for example a (2–4C)alkanoyl group (especially acetyl), a (1–4C)alkoxycarbonyl group (especially methoxycarbonyl, ethoxycarbonyl or tert-butoxycarbonyl), an arylmethoxycarbonyl group (especially benzyloxycarbonyl) or an aroyl group (especially benzoyl). The deprotection conditions for the above protecting groups necessarily vary with the choice of protecting group. Thus, for example, an acyl group such as an alkanoyl or alkoxycarbonyl or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-charcoal.

A suitable protecting group for a hydroxy group is, for example, an acyl group, for example a (2–4C)alkanoyl group (especially acetyl), an aroyl group (especially benzoyl) or an arylmethyl group (especially benzyl). The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-charcoal.

The starting materials of the formula $Ar^1$—$A^1$—$X^1$—H and of the formula II may be obtained by standard procedures of organic chemistry. Thus, for example, when a starting material of the formula $Ar^1$—SH is required, it may be obtained by, for example, the reaction of a heterocyclic moiety of the formula $Ar^1$—H as defined hereinbefore with a halosulphonylating agent such as, for example, chlorosulphonic acid, in a suitable solvent or diluent, for example dichloroethane or pyridine, and at a temperature in the range, for example 40° to 150° C., conveniently at or near 100° C. The intermediate of, for example, the formula $Ar^1$—$SO_2$—Cl so produced may be reduced to a compound of the formula $Ar^1$—SH by a conventional reducing agent such as, for example, a suitable reducing metallic salt such as a metallic halide, for example a stannous halide, conveniently stannous chloride, in a suitable solvent or diluent such as a (2–4C)alkanoic acid, for example acetic acid, and at a temperature in the range, for example, 40° to 150° C., conveniently in the range 80° to 100° C. Alternatively the reducing agent may be a suitable reducing metal, such as zinc or iron, in the presence of a strong acid, such as hydrochloric, sulphuric or phosphoric acid, and at a temperature in the range, for example 10 to 150° C., conveniently at or near 100° C. Alternatively the reducing agent may be a tri-(1–4C)alkylsilyl halide, conveniently trimethylsilyl iodide, in a suitable solvent or diluent such as methylene chloride and at a temperature at or near ambient temperature.

Conveniently intermediates of the formula II wherein Z, $Ar^2$, $R^1$, $R^2$ and $R^3$ have the meanings defined hereinbefore may be obtained by way of compounds of the formula Z—$Ar^2$—Y, wherein Z and $Ar^2$ have the meanings defined hereinbefore and Y is, for example, a halogeno, formyl, alkanoyl, nitrile or alkoxycarbonyl group, as illustrated in accompanying Scheme I (set out hereinafter).

It will also be appreciated that the intermediate of the formula II may conveniently be obtained from the compound of the formula Z—$Ar^2$—Y, as defined hereinbefore, by reversing the order of introduction of the groups $R^2$ and $R^3$ which is used in Scheme I.

(b) The coupling of a compound of the formula $Ar^1$—$A^1$—$X^1$—Z wherein Z is a displaceable group as defined hereinbefore, or alternatively, when $X^1$ is a thio group, Z may be a group of the formula $Ar^1$—$A^1$—$X^1$—, with an organometallic reagent of the formula III wherein M is an alkali metal or an alkaline earth metal such as lithium or calcium or M represents the magnesium halide portion of a conventional Grignard reagent; provided that, when there is an amino, alkylamino or hydroxy group in $Ar^1$, $R^2$ or $R^3$, any amino alkylamino or hydroxy group may be protected by a conventional protecting group as defined hereinbefore or alternatively any such group need not be protected, whereafter any undesired protecting group in $Ar^1$, $R^2$ or $R^3$ is removed by conventional means.

The coupling reaction is conveniently performed in a suitable inert solvent as defined hereinbefore and at a temperature in the range, for example, −80° to +50° C., conveniently in the range −80° C. to ambient temperature.

The preparation of starting materials of the formula $Ar^1$—$A^1$—$X^1$—Z and of the formula III is described within the accompanying non-limiting Examples which are provided for the purpose of illustration only. Alternatively such starting materials may be obtained by standard procedures of organic chemistry.

(c) The coupling, preferably in the presence of a suitable base as defined hereinbefore, of a compound of the formula IV with a compound of the formula $Ar^1$—$A^1$—Z wherein Z is a displaceable group as defined hereinbefore; provided that, when there is an amino, alkylamino or hydroxy group in $Ar^1$, $R^2$ or $R^3$, or , any amino, alkylamino or hydroxy group may be protected by a conventional protecting group as defined hereinbefore or alternatively any such group need not be protected, whereafter any undesired protecting group in $Ar^1$, $R^2$ or $R^3$ is removed by conventional means.

The coupling reaction is conveniently performed in a suitable inert solvent as defined hereinbefore and at a temperature in the range, for example, 10° to 150° C. conveniently at or near 100° C. The reaction may conveniently be performed in the presence of a suitable catalyst as defined hereinbefore.

The starting materials of the formula $Ar^1$—$A^1$—Z and of the formula IV may be obtained by standard procedures of organic chemistry. Starting materials of the formula IV are obtainable by analogous procedures to those illustrated in accompanying Scheme II (set out hereinafter) or by modifications thereto which are within the ordinary skill of an organic chemist.

A suitable protecting group $R^4$, as employed in Scheme II, is any one of the many such groups known in the art and includes any appropriate protecting group as defined hereinbefore. Examples of such groups are given in Scheme II. The conditions for the introduction and removal of such protecting groups are described in standard textbooks of organic chemistry such as, for example, "Protective Groups in Organic Synthesis" by T W Green (J Wiley and Sons, 1981).

(d) The alkylation, preferably in the presence of a suitable base as defined hereinbefore, of a compound of the formula V with a Compound of the formula $R^1$—Z, wherein $R^1$ and Z have the meanings defined hereinbefore; provided that, when there is an amino, imino, alkylamino or hydroxy group in $Ar^1$, $X^1$, $R^2$ or $R^3$ any amino, imino, alkylamino or hydroxy group may be protected by a conventional protecting group or alternatively any such group need not be protected, whereafter any undesired protecting group in $Ar^1$, $X^1$, $R^2$ or $R^3$ is removed by conventional means.

A suitable protecting group for an imino group is, for example, any of the protecting groups defined hereinbefore for an amino or alkylamino group.

The tertiary alcohol starting material of the formula V may be obtained by standard procedures of organic chemistry. The preparation of such starting materials is described within the accompanying non-limiting Examples which are provided for the purpose of illustration only. Conveniently, and as illustrated in accompanying Scheme III (set out hereinafter), intermediates of the formulae $Ar^1$—$A^1$—$X^1$—$Ar^2$—Y, wherein $Ar^1$, $A^1$, $X^1$ and $Ar^2$ have the meanings defined hereinbefore and Y is, for example, a halogeno, formyl, alkanoyl, nitrile or alkoxycarbonyl group may be utilised in the preparation of the tertiary alcohol starting material of the formula V.

(e) For the production of those compounds of the formula I wherein $R^1$ and $R^2$ together form a group of the formula —$A^2$—$X^2$—$A^3$— which, together with the oxygen atom to which $A^2$ is attached, defines a ring having 5 to 7 ring atoms and wherein $A^2$, $X^2$ and $A^3$ have the meanings defined hereinbefore, and wherein $R^3$ has the meaning defined hereinbefore; the cyclisation of a compound of the formula VI upon reaction with an appropriate aldehyde or ketone, or with a hemiacetal or acetal thereof, or with a compound of the formula Z—$A^2$—Z, wherein Z has the meaning defined hereinbefore; provided that, when there is an amino, imino, alkylamino or hydroxy group in $Ar^1$ or $X^1$, any amino, imino, alkylamino or hydroxy group is protected by a conventional protecting group, whereafter any undesired protecting group in $Ar^1$ or $X^1$ is removed by conventional means.

The cyclisation of a compound of the formula VI with an appropriate aldehyde or ketone, or with a hemiacetal or acetal thereof, is conveniently carried out in the presence of a suitable acid. A suitable acid for the cyclisation reaction is, for example, an inorganic acid such as hydrochloric, sulphuric or phosphoric acid, or, for example, an organic acid such as p-toluenesulphonic acid or trifluoroacetic acid. The cyclisation reaction is conveniently performed in a suitable inert solvent or diluent, for example 1,2-dimethoxyethane or tetrahydrofuran. Preferably the reaction is performed using the appropriate aldehyde or ketone, or a hemiacetal or acetal derivative thereof, as both a reactant and diluent. The cyclisation is effected at a temperature in the range, for example, 20° to 150° C., conveniently at or near the boiling point of the diluent or solvent.

The cyclisation of a compound of the formula VI with a compound of the formula Z—$A^2$—Z is conveniently carried out in the presence of a suitable base as defined hereinbefore.

The tertiary alcohol starting material of the formula VI may be obtained by standard procedures of organic chemistry. Conveniently, and as illustrated in accompanying Scheme IV (set out hereinafter), intermediates of the formula $Ar^1$—$A^1$—$X^1$—$Ar^2$—Y, wherein $Ar^1$, $A^1$, $X^1$, $Ar^2$ and Y have the meanings defined hereinbefore, may be utilised in the preparation of the tertiary alcohol starting material of the formula VI.

A suitable protecting group $R^4$, as defined hereinbefore, is employed.

(f) For the production of those compounds of the formula I wherein $X^1$ is a sulphinyl or sulphonyl group, wherein and $R^2$, $R^3$ together form a group of the formula —$A^2$—$X^2$—$A^3$— and $X^2$ is a sulphinyl or sulphonyl group or wherein $R^1$ and $R^2$ together form a group of the formula —$A^2$—$X^2$—$A^3$— and $X^2$ is a sulphinyl or sulphonyl group, the oxidation of a compound of the formula I wherein $X^1$ is a thio group, wherein $R^2$ and $R^3$ together form a group of the formula —$A^2$—$X^2$—$A^3$— and $X^2$ is a thio group or wherein $R^1$ and $R^2$ together form a group of the formula —$A^2$—$X^2$—$A^3$— and $X^2$ is a thio group.

A suitable oxidising agent is, for example, any agent known in the art for the oxidation of thio to sulphinyl and/or sulphonyl, for example, hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinum. The oxidation is generally carried out under as mild conditions as possible and with the required stoichiometric amount of oxidising agent in order to reduce the risk of over oxidation and damage to other functional groups. In general the reaction is carried out in a suitable solvent or diluent such as methylene chloride, chloroform, acetone, tetrahydrofuran or tert-butyl methyl ether and at a temperature, for example, at or near ambient temperature, that is in the range 15° to 35° C. When a compound carrying a sulphinyl group is required a milder oxidising agent may also be used, for example sodium or potassium metaperiodate, conveniently in a polar solvent such as acetic acid or ethanol. It will be appreciated that when a compound of the formula I containing a sulphonyl group is required, it may be obtained by oxidation of the corresponding sulphinyl compound as well as of the corresponding thio compound.

(g) For the production of those compounds of the formula I wherein $Ar^1$ bears an alkyl or substituted alkyl substituent on an available nitrogen atom, or wherein $Ar^2$ bears an alkoxy substituent, the alkylation of a compound of the formula I wherein $Ar^1$ bears a hydrogen atom on said available nitrogen atom, or wherein $Ar^2$ bears a hydroxy substituent.

A suitable alkylating agent is, for example, any agent known in the art for the alkylation of an available nitrogen atom, or of hydroxy to alkoxy, for example an alkyl or substituted alkyl halide, for example a (1–4C)alkyl chloride, bromide or iodide or a substituted (1–4C)alkyl chloride, bromide or iodide, in the presence of a suitable base. A suitable base for the alkylation reaction is, for example, an alkali or alkaline earth metal carbonate, sodium hydroxide, potassium hydroxide, sodium hydride or potassium hydride. The alkylation reaction is preferably performed in a suitable inert solvent or diluent, for example N,N-dimethylformamide, dimethylsulphoxide, acetone, 1,2-dimethoxyethane or tetrahydrofuran, and at a temperature in the range, for example 10° to 150° C., conveniently at or near ambient temperature.

(h) For the production of those compounds of the formula I wherein $Ar^1$ bears one or more thioxo substituents, the reaction of a heterocyclene derivative of the formula I wherein $Ar^1$ bears one or more oxo substituents with a thiation reagent such that each oxo substituent is converted into a thioxo substituent; provided that, when there is an amino, imino, alkylamino or hydroxy group in $Ar^1$, $X^1$, $Ar^2$, $R^2$ or $R^3$ or any such group may be protected by a conventional protecting group or alternatively any such group need not be protected, whereafter any undesired protecting group in $Ar^1$, $X^1$, $Ar^2$, $R^2$ and $R^3$ is removed by conventional means.

A suitable thiation reagent is, for example, any agent known in the art for the conversion of an oxo group to a thioxo group such as, for example, 2,4-bis-(4-methoxyphenyl)-1,3-dithia-2,4 -diphosphetane-2,4-disulphide (Lawesson's Reagent) or phosphorus pentasulphide. The thiation reaction is generally carried out with the required stoichiometric amount of thiation reagent in order to reduce the risk of damage to other functional groups. In general the reaction is carried out in a suitable solvent or diluent such as toluene, xylene or tetrahydrofuran and at a temperature, for example, at or near the reflux temperature of the solvent or diluent, that is in the range 65° to 150° C.

(i) For the production of those compounds of the formula I wherein $Ar^1$ bears one or more optionally substituted α-hydroxybenzyl substituents, the reaction of a heterocyclene derivative of the formula I wherein $Ar^1$ bears one or more halogeno substituents with a metal such as magnesium or with a (1–4C)alkyl-lithium reagent such as n-butyllithium to form an organometallic reagent which is reacted with an optionally substituted benzaldehyde; provided that, when there is an amino, imino, alkylamino or hydroxy group in $Ar^1$, $X^1$, $Ar^2$, $R^2$ or $R^3$ any such group may be protected by a conventional protecting group or alternatively any such group need not be protected, whereafter any undesired protecting group in $Ar^1$, $X^1$, $Ar^2$, $R^2$ and $R^3$ is removed by conventional means.

(j) For the production of those compounds of the formula I wherein $Ar^1$ bears one or more optionally-substituted benzoyl substituents, the oxidation of a heterocyclene derivative of the formula I wherein $Ar^1$ bears one or more optionally substituted α-hydroxybenzyl substituents.

A suitable oxidising agent is, for example, any agent known in the art for the oxidation of a secondary alcohol to a ketone, for example, a chromium reagent (such as pyridinium chlorochromate). In general the oxidation is carried out in a suitable solvent or diluent such as methylene chloride or chloroform and at a temperature, for example at or near ambient temperature, that is in the range 15° to 35° C.

When a pharmaceutically-acceptable salt of a novel compound of the formula I is required, it may be obtained, for example, by reaction of said compound with a suitable acid or base using a conventional procedure. When an optically active form of a compound of the formula I is required, it may be obtained by carrying out one of the aforesaid procedures using an optically active starting material, or by resolution of a racemic form of said compound using a conventional procedure.

Many of the intermediates defined herein are novel, for example those of the formulae V and VI and these are provided as a further feature of the invention.

As stated previously, the novel compounds of the formula I are inhibitors of the enzyme 5-LO. The effects of this inhibition may be demonstrated using one or more of the standard procedures set out below:

a) An in vitro spectrophotometric enzyme assay system, which assesses the inhibitory properties of a test compound in a cell free system using 5-LO isolated from guinea pig neutrophils and as described by D. Aharony and R. L. Stein (*J. Biol. Chem.*, 1986, 261(25), 11512–11519). This test provides a measure of the intrinsic inhibitory properties of a test compound against soluble 5-LO in an extracellular environment.

b) An in vitro assay system involving incubating a test compound with heparinised human blood, prior to challenge with the calcium ionophore A23187 and then indirectly measuring the inhibitory effects on 5-LO by assaying the amount of $LTB_4$ using specific radioimmunoassays described by Carey and Forder (F. Carey and R. A. Forder, *Prostaglandins, Leukotrienes Med.*, 1986, 22, 57; *Prostaglandins*, 1984, 28, 666; *Brit. J. Pharmacol.* 1985, 84, 34P) which involve the use of a protein-$LTB_4$ conjugate produced using the procedure of Young et alia (*Prostaglandins*, 1983, 26(4), 605–613). The effects of a test compound on the enzyme cyclooxygenase (which is involved in the alternative metabolic pathway for arachidonic acid and gives rise to prostaglandins, thromboxanes and related metabolites) may be measured at the same time using the specific radioimmunoassay for thromboxane $B_2$ ($TxB_2$) described by Carey and Forder (see above). This test provides an indication of the effects of a test compound against 5-LO and also cyclooxygenase in the presence of blood cells and proteins. It permits the selectivity of the inhibitory effect on 5-LO or cyclooxygenase to be assessed.

c) An ex vivo assay system, which is a variation of test b) above, involving administration of a test compound (usually orally as the suspension produced when a solution of the test compound in dimethylsulphoxide is added to carboxymethylcellulose), blood collection, heparinisation, challenge with A23187 and radioimmunoassay of $LTB_4$ and $TxB_2$. This test provides an indication of the bioavailability of a test compound as an inhibitor of 5-LO or cyclooxygenase.

d) An in vitro assay system involving the measurement of the inhibitory properties of a test compound against the liberation of $LTC_4$ and $PGE_2$ induced by zymosan on mouse resident peritoneal macrophages, using the procedure of Humes (J. L. Humes et alia, *Biochem. Pharmacol.*, 1983, 32, 2319–2322) and conventional radioimmunoassay systems to measure $LTC_4$ and $PGE_2$. This test provides an indication of inhibitory effects against 5-LO and cyclooxygenase in a non-proteinaceous system.

e) An in vivo system involving the measurement of the effects of a test compound in inhibiting the inflammatory response to arachidonic acid in the rabbit skin model developed by D. Aked et alia (*Brit. J. Pharmacol.,* 1986, 89,431–438). This test provides an in vivo model for 5-LO inhibitors administered optically or orally.

f) An in vivo system involving measuring the effects of a test compound administered orally or intravenously on a leukotriene dependent bronchoconstriction induced by an antigen challenge in guinea pigs pre-dosed with an antihistamine (mepyramine), a β-adrenergic blocking agent (propranolol) and a cyclooxygenase inhibitor (indomethacin), using the procedure of W. H. Anderson et alia (*British J. Pharmacology,* 1983, 78(1), 67–574). This test provides a further in vivo test for detecting 5-LO inhibitors.

g) An in vivo system involving measuring the effects of a test compound administered orally against the liberation of $LTB_4$ induced by zymosan within an air pouch generated within the subcutaneous tissue of the back of male rats. The rats are anaesthetised and air pouches are formed by the injection of sterile air (20 ml). A further injection of air (10 ml) is similarly given after 3 days. At 6 days after the initial air injection the test compound is administered (usually orally as the suspension produced when a solution of the test compound in dimethylsulphoxide is added to hydroxypropylmethylcellulose), followed by the intrapouch injection of zymosan (1 ml of a 1% suspension in physiological saline). After 3 hours the rats are killed, the air pouches are lavaged with physiological saline, and the specific radioimmunoassay described above is used to assay $LTB_4$ in the washings. This test provides an indication of inhibitory effects against 5-LO in an inflammatory milieu. Although the pharmacological properties of the compounds of the formula I vary with structural changes as expected, in general compounds of the formula I possess 5-LO inhibitory effects at the following concentrations or doses in one or more of the above tests a)–f):

Test a): $IC_{50}$ in the range, for example, 0.01–30 µM;

Test b): $IC_{50}$ ($LTB_4$) in the range, for example, 0.01–40 µM, $IC_{50}$ ($TxB_2$) in the range, for example, 40–200 µM;

Test c): oral $ED_{50}$($LTB_4$) in the range, for example, 0.1–100 mg/kg;

Test d): $IC_{50}$ ($LTC_4$) in the range, for example, 0.001–1 µM, $IC_{50}$ ($PGE_2$) in the range, for example, 20–1000 µM;

Test e): inhibition of inflammation in the range, for example, 0.3–100 µg intradermally;

Test f): $ED_{50}$ in the range, for example, 0.5–10 mg/kg i.v.;

Test g): oral $ED_{50}$($LTB_4$) in the range, for example, 0.1–50 mg/kg.

No overt toxicity or other untoward effects are present in tests c), e), f) and/or g) when compounds of the formula I are administered at several multiples of their minimum inhibitory dose or concentration.

Thus, by way of example, the compound 4-[5-(4-tert-butylphenylthio)thien- 2-yl]-4-methoxytetrahydropyran has an $IC_{50}$ of 0.15 µM against $LTB_4$ in test b), and an oral $ED_{50}$ of 1.5 mg/kg versus $LTB_4$ in test g); and the compound 4-methoxy-4-[5-(1-methyl-2-oxo-1,2,3,4 -tetrahydroquinolin-6-ylthio)thien-2-yl]tetrahydropyran has an $IC_{50}$ of 0.04 µM against $LTB_4$ in test b) and an oral $ED_{50}$ of <1.5 mg/kg versus $LTB_4$ in test g). In general those compounds of the formula I which are particularly preferred have an $IC_{50}$ of <1 µM against $LTB_4$ in test b), and an oral $ED_{50}$ of <100 mg/kg against $LTB_4$ in tests c) and/or g).

These compounds are examples of compounds of the invention which show selective inhibitory properties for 5-LO as opposed to cyclooxygenase, which selective properties are expected to impart improved therapeutic properties, for example, a reduction in or freedom from the gastrointestinal side-effects frequently associated with cyclooxygenase inhibitors such as indomethacin.

According to a further feature of the invention there is provided a pharmaceutical composition which comprises a heterocyclene derivative of the formula I, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. In general the above compositions may be prepared in a conventional manner using conventional excipients.

The amount of active ingredient (that is a heterocyclene derivative of the formula I, or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient.

According to a further feature of the invention there is provided a heterocyclene derivative of the formula I, or a pharmaceutically-acceptable salt thereof, for use in a method of Treatment of the human or animal body by therapy.

The invention also includes a method of treating a disease or medical condition mediated alone or in part by one or more leukotrienes which comprises administering to a warm-blooded animal requiring such treatment an effective amount of an active ingredient as defined above. The invention also provides the use of such an active ingredient in the production of a new medicament for use in a leukotriene mediated disease or medical condition.

The size of the dose for therapeutic or prophylactic purposes of a compound of the formula I will naturally vary according to the nature and severity of the conditions, the age and sex of the animal or patient and the route of administration, according to well known principles of medicine. As mentioned above, compounds of the formula I are useful in treating those allergic and inflammatory conditions which are due alone or in part to the effects of the metabolites of arachidonic acid arising by the linear (5-LO catalysed) pathway and in particular the leukotrienes, the production of which is mediated by 5-LO. As previously mentioned, such conditions include, for example, asthmatic conditions, allergic reactions, allergic rhinitis, allergic shock, psoriasis, atopic dermatitis, cardiovascular and cerebrovascular disorders of an inflammatory nature, arthritic and inflammatory joint disease, and inflammatory bowel diseases.

In using a compound of the formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used.

Although the compounds of the formula I are primarily of value as therapeutic agents for use in warm-blooded animals (including man), they are also useful whenever it is required to inhibit the enzyme 5-LO. Thus, they are useful as pharmacological standards for use in the development of new biological tests and in the search for new pharmacological agents.

By virtue of their effects on leukotriene production, the compounds of the formula I have certain cytoprotective effects, for example they are useful in reducing or suppressing certain of the adverse gastrointestinal effects of the cyclooxygenase inhibitory non-steroidal anti-inflammatory agents (NSAIA), such as indomethacin, acetylsalicylic acid, ibuprofen, sulindac, tolmetin and piroxicam. Furthermore, co-administration of a 5-LO inhibitor of the formula I with a NSAIA can result in a reduction in the quantity of the latter agent needed to produce a therapeutic effect, thereby reducing the likelihood of adverse side-effects. According to a further feature of the invention there is provided a pharmaceutical composition which comprises a heterocyclene derivative of the formula I, or a pharmaceutically-acceptable salt thereof as defined hereinbefore, in conjunction or admixture with a cyclooxygenase inhibitory non-steroidal anti-inflammatory agent (such as mentioned above), and a pharmaceutically-acceptable diluent or carrier.

The cytoprotective effects of the compounds of the formula I may be demonstrated, for example in a standard laboratory model which assesses protection against indomethacin-induced or ethanol-induced ulceration in the gastrointestinal tract of rats.

The compositions of the invention may in addition contain one or more therapeutic or prophylactic agents known to be of value for the disease under treatment. Thus, for example a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an anti-histamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition.

The invention will now be illustrated in the following non-limiting Examples in which, unless otherwise stated:

(i) evaporations were carried out by rotary evaporation in vacuo and work-up procedures were carried out after removal of residual solids by filtration;

(ii) operations were carried out at room temperature, that is in the range 18°–25° and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Meck, Darmstadt, W. Germany;

(iv) yields are given for illustration only and are not necessarily the maximum attainable;

(v) the end-products of the formula I have satisfactory microanalyses and their structures were confirmed by NMR and mass spectral techniques;

(vi) intermediates were not generally fully characterised and purity was assessed by thin layer chromatographic, infra-red (IR) or NMR analysis;

(vii) melting points are uncorrected and were determined using a Merrier SP62 automatic melting point apparatus or an oil-bath apparatus; melting points for the end-products of the formula I were determined after crystallisation from a conventional organic solvent such as ethanol, methanol, acetone, ether or hexane, alone or in admixture; and (viii) the following abbreviations have been used:

| THF | tetrahydrofuran; |
|---|---|
| DMSO | dimethylsulphoxide; |
| DMF | N,N-dimethylformamide; |
| DMA | N,N-dimethylacetamide. |

EXAMPLE 1

Sodium hydride (60% w/w dispersion in mineral oil, 0.065 g) was added portionwise to a solution of 4-[5-(4-tert-butylphenylthio)thien- 2-yl]-4-hydroxytetrahydropyran (0.285 g) in THF (10 ml) and the mixture was stirred at ambient temperature for 30 minutes. Methyl iodide (0.213 g) was added and the mixture was stirred at ambient temperature for 12 hours. The mixture was poured into a cold saturated aqueous ammonium chloride solution and extracted with ethyl acetate. The organic phase was dried (MgSO$_4$) and evaporated. The residue was purified by column chromatography using a 19:1 v/v mixture of methylene chloride and diethyl ether as eluent. There was thus obtained 4-[5-(tert-butylphenylthio)thien-2-yl]-4-methoxytetrahydropyran (0.275 g, 95%), as an oil.

NMR Spectrum (CDCl$_3$, δ values) 1.3 (s, 9H), 1.9–2.15 (m, 4H), 3.05 (s, 3H), 3.7–3.9 (m, 4H), 6.8–7.4 (m, 6H).

The 4-[5-(4-tert-butylphenylthio)thien-2-yl]-4-hydroxytetrahydropyran used as a starting material was obtained as follows:

A mixture of the copper (I) salt of 4-tert-butylphenylthiol [2.5 g; obtained by heating a mixture of cuprous oxide (4.3 g), 4-tert-butylphenylthiol (5 g) and ethanol (25 ml) to reflux for 3 hours, and filtration], 2-iodothiophene (2.3 g), pyridine (0.5 ml) and quinoline (10 ml) was heated to 200° C. for 2.5 hours. The mixture was cooled to ambient temperature and partitioned between 6N aqueous hydrochloric acid and ethyl acetate. The organic layer was dried (MgSO$_4$) and evaporated. The residue was purified by column chromatography using a 19:1 v/v mixture of methylene chloride and petroleum ether (b.p. 40°–60° C.) as eluent. There was thus obtained 4-tert-butylphenyl 2-thienyl sulphide (1.15 g, 43%) as an oil.

n-Butyl-lithium (1.6M in hexane, 1.25 ml) was added dropwise to a solution of the product so obtained (0.5 g) in THF (10 ml) which had been cooled to –30° C. The mixture was stirred at –20° C. for 1 hour. The mixture was cooled to –78° C. and tetrahydropyran-4-one (0.2 g) was added dropwise. The mixture was stirred for 58 hours and allowed to warm to ambient temperature. The mixture was partitioned between a cold saturated aqueous ammonium chloride solution and ethyl acetate. The organic layer was dried (MgSO₄) and evaporated. The residue was purified by column chromatography using a 9:1 v/v mixture of methylene chloride and diethyl ether as eluent. There was thus obtained the required starting material (0.305 g, 44%), m.p. 112° C.

EXAMPLE 2

Using the procedure described in Example 1, 4-hydroxy-4-[5-(naphth-2-ylthio)thien-2-yl]tetrahydropyran was reacted with methyl iodide to give 4-methoxy-4-[5-(naphth-2-ylthio)thien-2-yl]tetrahydropyran in 81% yield, m.p. 70° C.

The 4-hydroxy-4-[5-(naphth-2-ylthio)thien-2-yl]tetrahydropyran used as a starting material was obtained as follows:

The procedures described in the portion of Example 1 which is concerned with the preparation of starting materials were repeated except that 2-naphthalenethiol was used in place of 4-tert-butylphenylthiol and 2-bromothiophene was used in place of 2-iodothiophene. There were thus obtained in turn: 2-naphthyl 2-thienyl sulphide in 45% yield, m.p. 77°–79° C.; and the required starting material in 67% yield, m.p. 130° C.

EXAMPLE 3

Using the procedure described in Example 1, 4-hydroxy-4-[5-(naphth-2-ylthio)fur-2-yl]tetrahydropyran was reacted with methyl iodide to give 4-methoxy-4-[5-(naphth-2-ylthio)fur-2-yl]tetrahydropyran in 92% yield as an oil.

NMR Spectrum (CD₃COCD₃, δ values) 1.9–2.3 (m, 4H), 3.05 (s, 3H), 3.45–3.9 (m, 4H), 6.6 (d, 1H), 6.9 (d, 1H), 7.25–8.0 (m, 7H).

The 4-hydroxy-4-[5-(naphth-2-ylthio)fur-2-yl]tetrahydropyran used as a starting material was obtained as follows:

A mixture of the copper (I) salt of 2-naphthalenethiol [2.1 g; obtained by heating a mixture of cuprous oxide (0.71 g), 2-naphthalenethiol (1.6 g) and ethanol (10 ml) to reflux for 3 hours and filtration], 2-bromofuran (1.47 g; *Tetrahedron*, 1985, 41, 1919), pyridine (0.5 ml) and quinoline (7 ml) was heated to 200° C. for 3 hours. The mixture was poured onto a mixture of crushed ice and 6N aqueous hydrochloric acid and extracted with ethyl acetate. The organic phase was washed with water and brine, dried (MgSO₄) and evaporated. The residue was purified by column chromatography using a 19:1 v/v mixture of petroleum ether (b.p. 40°–60° C.) and methylene chloride as eluent. There was thus obtained 2-furyl 2-naphthyl sulphide (1.15 g) in 52% yield as an oil.

n-Butyl-lithium (1.6M in hexane, 1.9 ml) was added dropwise to a solution of a portion (0.68 g) of the product so obtained in THF (5 ml) which had been cooled to 0° C. in an ice-bath. The mixture was stirred at 0° C. for 2.5 hours then tetrahydropyran-4-one (0.3 g) was added dropwise. The mixture was stirred and allowed to warm slowly to 20° C. The mixture was stirred at ambient temperature for 12 hours. The mixture was partitioned between a cold saturated aqueous ammonium chloride solution and ethyl acetate. The organic layer was dried (MgSO₄) and evaporated. The residue was purified by column chromatography using a 9:1 v/v mixture of methylene chloride and diethyl ether as eluent. There was thus obtained the required starting material (0.5 g, 51%), m.p. 120°–122° C.

EXAMPLE 4

Using the procedure described in Example 1, (2RS,3RS)-3-hydroxy-2-methyl-3-[5-(naphth-2-ylthio)thien-2-yl]tetrahydrofuran was reacted with methyl iodide to give (2RS,3RS)-3-methoxy-2-methyl-3-[5-(naphth-2-ylthio)thien-2-yl]tetrahydrofuran in 75% yield as an oil.

NMR Spectrum (CDCl₃, δ values) 1.29 (d, 3H), 2.29–2.60 (m, 2H), 3.23 (s, 3H), 3.7–4.2 (m, 3H), 6.93–7.78 (m, 9H).

The (2RS,3RS)-3-hydroxy-2-methyl-3-[5-(naphth-2-ylthio)thien-2-yl]tetrahydrofuran used as a starting material was obtained as follows:

n-Butyl-lithium (2.5M in hexane, 0.512 ml) was added dropwise to a solution of 2-naphthyl 2-thienyl sulphide (0.31 g) in THF (8 ml) which had been cooled to −78° C. The mixture was allowed to warm to 0° C. and was stirred at that temperature for 1 hour. The mixture was cooled to −60° C. and 2-methyltetrahydrofuran-3-one (0.128 g) was added dropwise. The mixture was allowed to warm to ambient temperature and was stirred for 12 hours. The mixture was partitioned between a cold saturated aqueous ammonium chloride solution and ethyl acetate. The organic layer was dried (MgSO₄) and evaporated. The residue was purified by column chromatography using a 23:2 v/v mixture of methylene chloride and diethyl ether as eluent. There was thus obtained the required starting material (0 23 g, 52%), m.p 105°–107° C., having the 2-methyl and 3-hydroxy groups in a cis-relationship.

EXAMPLE 5

A solution of 4-(5-bromothien-2-yl)-4-methoxytetrahydropyran (0.415 g) in THF (1.5 ml) was added dropwise to n-butyl-lithium (1.5M in hexane, 1 ml) which had been cooled to −78° C. and the mixture was stirred at −78° C. for 2 hours. A solution of di-(4-bromophenyl) disulphide (0.564 g) in THF (1.5 ml) was added and the mixture was stirred at −78° C. for 3 hours. The mixture was allowed to warm to ambient temperature and was stirred for 16 hours. The mixture was poured into a cold aqueous ammonium chloride solution (15% w/v) and extracted with ethyl acetate. The organic phase was washed with water, dried (MgSO₄) and evaporated. The residue was purified by column chromatography using initially a 9:1 v/v mixture of petroleum ether (b.p. 40°–60° C.) and ethyl acetate and then a 4:1 v/v mixture of petroleum ether and ethyl acetate as eluent. There was thus obtained 4-[5-(4-bromophenylthio)thien-2-yl]-4-methoxytetrahydropyran (0.217 g, 38%), m.p. 62°–63° C.

NMR Spectrum (CDCl₃, δ values) 2.0–2.4 (m, 4H), 3.06 (s, 3H), 3.6–3.85 (m, 4H), 7.05–7.6 (m, 6H).

The 4-(5-bromothien-2-yl)-4-methoxytetrahydropyran used as a starting material was obtained as follows:

n-Butyl-lithium (1.6M in hexane, 31 ml) was added dropwise to a stirred solution of 2,5-dibromothiophene (12.1 g) in THF (40 ml) which had been cooled to −40° C. The mixture was allowed to warm to −20° C. and was stirred at this temperature for 1 hour. The mixture was cooled to −78° C. and tetrahydropyran-4-one (5 g) was added dropwise. The mixture was allowed to warm to ambient temperature and stirred for 12 hours. The mixture was poured into a cold aqueous ammonium chloride solution (15% w/v) and extracted with ethyl acetate. The organic phase was washed with water, dried (MgSO₄) and evaporated. The residue was purified by column chromatography using a 17:3 v/v mixture of methylene chloride and diethyl ether as eluent. There was thus obtained 4-(5-bromothien-2-yl)-4-hydroxytetrahydropyran (4.16 g, 32%), m.p. 100°–102° C.

A portion (2.48 g) of the product so obtained was reacted with methyl iodide using a similar procedure to that described in Example 1. There was thus obtained the required starting material (2.1 g, 80%), m.p. 57°–59° C.

NMR Spectrum (CDCl$_3$, δ values) 1.9–2.2 (m, 4H), 3.06 (s, 3H), 3.6–3.85 (m, 4H), 6.87 (d, 1H), 7.03 (d, 1H).

The di-(4-bromophenyl) disulphide used as a starting material was obtained as follows using a method based upon that in *J. Org. Chem.*, 1963, 28, 3246:

A solution of 4-bromophenylthiol (2 g) in DMSO (5 ml) was heated to 100° C. for 16 hours. The mixture was poured onto a mixture of ice and water. The precipitate was isolated and dried. There was thus obtained the required starting material (1.9 g, 95%).

EXAMPLE 6 n-Butyl-lithium (1.6M in hexane, 1.23 ml) was added dropwise to a stirred solution of di-isopropylamine (0.275 ml) in THF (2 ml) which had been cooled to −78° C. and the mixture was stirred for 20 minutes. A solution of 4-methoxy-4-(3-thienyl)tetrahydropyran (0.37 g) in THF (1.5 ml) was added dropwise. The resultant mixture was allotted to warm slowly to −30° C. over approximately 2 hours. The mixture was recooled to −70° C. and a solution of di-(4-tert-butylphenyl) disulphide (0.595 g) in THF (2 ml) was added dropwise. The mixture was allowed to warm to ambient temperature and was stirred for 12 hours. The mixture was poured into a cold aqueous ammonium chloride solution (15% w/v) and extracted with methylene chloride. The organic phase was washed with water, dried (MgSO$_4$) and evaporated. The residue was purified by column chromatography using increasingly polar mixtures of methylene chloride and diethyl ether as eluent. There was thus obtained 4-[2-(4-tert-butylphenylthio)thien-4-yl]-4-methoxytetrahydropyran (0.133 g, 20%) as an oil.

NMR Spectrum (CDCl$_3$, δ values) 1.28 (s, 9H), 1.9–2.15 (m, 4H), 3.03 (s, 3H), 3.7–3.95 (m, 4H), 7.0–7.45 (m, 6H).

The 4-methoxy-4-(3-thienyl)tetrahydropyran used as a starting material was obtained as follows:

Using the procedure described in *Bull. Soc. Chim. Fr.*, 1955, 84, 424, a Grignard reagent was prepared by heating to reflux a mixture of magnesium (4.45 g), 3-bromothiophene (10 g), ethyl bromide (14 ml) and diethyl ether (200 ml) for 1 hour. The mixture was cooled to ambient temperature and tetrahydropyran-4-one (1.2 ml) was added dropwise. The mixture was stirred at ambient temperature for 12 hours. The mixture was poured into a cold aqueous ammonium chloride solution (15% w/v) and extracted with diethyl ether. The organic phase was washed with water, dried (MgSO$_4$) and evaporated. The residue was purified by column chromatography using a 9:1 v/v mixture of methylene chloride and diethyl ether as eluent. There was thus obtained 4-hydroxy-4-(3-thienyl)tetrahydropyran (0.5 g, 20%), m.p. 87° C. (recrystallised from a mixture of pentane and diethyl ether).

A portion (0.45 g) of the product so obtained was reacted with methyl iodide using a similar procedure to that described in Example 1. There was thus obtained the required starting material (0.468 g, 97%), m.p. 44° C.

The di-(4-tert-butylphenyl) disulphide used as a starting material was obtained from 4-tert-butylphenylthiol using a similar procedure to that described in the portion of Example 5 which is concerned with the preparation of di-(4-bromophenyl) disulphide. There was thus obtained the required disulphide in 96% yield, m.p. 90° C. (recrystallised from ethanol).

EXAMPLE 7

Using the procedure described in Example 5, 4-(5-bromothien-2-yl)-4-methoxytetrahydropyran was reacted with di-(1-methyl-2-oxo-1,2,3,4-tetrahydroquinolin-6-yl) disulphide to give 4-methoxy-4-[5-(1-methyl-2-oxo-I,2,3,4-tetrahydroquinolin-6 -ylthio)thien-2-yl]tetrahydropyran in 55% yield, m.p. 84°–86° C.

NMR Spectrum (CD$_3$COCD$_3$, δ values) 1.95–2.20 (m, 4H), 2.4–3.0 (m, 4H), 3.06 (s, 3H), 3.27 (s, 3H), 3.65–3.80 (m, 4H), 7.0–7.3 (m, 5H).

The di-(1-methyl-2-oxo-1,2,3,4-tetrahydroquinolin-6-yl) disulphide used as a starting material was obtained as follows:

A mixture of 1-methyl-1,2-dihydroquinolin-2-one (8 g), 10% palladium-on-charcoal catalyst (2 g) and ethanol (60 ml) was stirred under a pressure of 3.5 atmospheres of hydrogen for 24 hours. The mixture was filtered and evaporated. The residue was purified by column chromatography using a 9:1 v/v mixture of methylene chloride and diethyl ether as eluent. There was thus obtained 1-methyl-1,2,3,4-tetrahydroquinolin-2-one (7.88 g, 98%) as an oil.

A portion (1.6 g) of the product so obtained was added dropwise to chlorosulphonic acid (8 ml) and the mixture was heated to 80° C. for 2.5 hours. The mixture was cooled to ambient temperature, poured onto a mixture of ice and water and extracted with ethyl acetate. The organic phase was washed with water, dried (MgSO$_4$) and evaporated to give 1-methyl-2-oxo-1,2,3,4-tetrahydroquinolin-6-ylsulphonyl chloride (1.97 g, 76%), m.p. 137°–139° C.

NMR Spectrum (CDCl$_3$, δ values) 2.7–3.25 (m, 4H), 3.41 (s, 3H), 7.13 (d, 1H), 7.80–8.10 (m, 2H).

Trimethylsilyl iodide (5 g) was added dropwise to a solution of a portion (1.2 g) of the product so obtained in methylene chloride (40 ml) and the mixture was stirred at ambient temperature for 16 hours. The mixture was washed with a saturated aqueous sodium bicarbonate solution and with a saturated aqueous sodium sulphite solution, dried (MgSO$_4$) and evaporated. The residue was purified by column chromatography using a 9:1 v/v mixture of methylene chloride and diethyl ether as eluent. There was thus obtained the required disulphide (0.418 g, 43%), m.p. 130° C.

NMR Spectrum (CD$_3$COCD$_3$) 2.40–3.0 (m, 4H), 3.26 (s, 3H), 6.84 (d, 1H), 7.15–7.40 (m, 2H).

EXAMPLE 8

Using the procedure described in Example 5, 4-(5-bromothien-2-yl)-4-methoxytetrahydropyran was reacted with di-(1-methyl-2-oxo-1,2-dihydroquinolin-6-yl) disulphide to give 4-methoxy-4-[5-(1-methyl-2-oxo-1,2-dihydroquinolin-6-ylthio)thien-2-yl] tetrahydropyran in 19% yield, m.p. 119°–120° C.

NMR Spectrum (CD$_3$COCD$_3$) 1.95–2.15 (m, 4H), 3.06 (s, 3H), 3.64–3.8 (m, 4H), 3.69 (s, 3H), 6.6 (d, 1H), 7.05 (d, 1H), 7.27 (d, 1H), 7.5–7.7 (m, 3H), 7.75 (d, 1H).

The di-(1-methyl-2-oxo-1,2-dihydroquinolin-6-yl) disulphide used as a starting material was obtained from 1-methyl-1,2 -dihydroquinolin-2-one using the procedures described in the portion of Example 7 which is concerned with the preparation of di-(1-methyl-2 -oxo-1,2,3,4-tetrahydroquinolin-6-yl) disulphide except that the hydrogenation step was not required. There was thus obtained the required starting material in 83% yield, m.p. 222°–223° C.

EXAMPLE 9

Using the procedure described in Example 5, 4-(5-bromothien-2-yl)-4-methoxytetrahydropyran was reacted with di-(1-methyl-2-thioxo-1,2,3,4-tetrahydroquinolin-6-yl) disulphide to give 4-methoxy-4-[5-(1-methyl-2-thioxo-1,2,3,4-tetrahydroquinolin-6 -ylthio)thien-2-yl]tetrahydropyran in 62% yield, m.p. 100°–102° C.

NMR Spectrum (CD$_3$COCD$_3$, δ values) 2.0–2.2 (m, 4H), 2.7–3.3 (m, 4H), 3.07 (s, 3H), 3.65–3.85 (m, 4H), 3.87 (s, 3H), 7.04–7.30 (m, 5H).

The di-(1-methyl-2-thioxo-1,2,3,4-tetrahydroquinolin-6-yl) disulphide used as a starting material was obtained as follows:

A mixture of di-(1-methyl-2-oxo-1,2,3,4-tetrahydroquinolin 6-yl) disulphide (1 g), 2,4-bis(4-methoxyphenyl)-1,3-dithia-2,4 -diphosphetane-2,4-disulphide (Lawesson's Reagent, 0.65 g) and toluene (10 ml) was heated to reflux for 1 hour. The mixture was evaporated and the residue was purified by column chromatography using methylene chloride as eluent. There was thus obtained the required starting material (0.86 g, 79%), m.p. 180°–182° C.

EXAMPLE 10

Using the procedure described in Example 5, 4-(5-bromothien- 2-yl)-4-methoxytetrahydropyran was reacted with di-(4-methyl-3-oxo- 2,3-dihydro-4H-1,4-benzoxazin-7-yl) disulphide to give 4-methoxy-4-[ 5-(4-methyl-3-oxo-2,3-dihydro-4H-1,4-benzoxazin-7-ylthio)thien-2-yl] tetrahydropyran in 28% yield, m.p. 65°–69° C.

NMR Spectrum (CD$_3$COCD$_3$, δ values) 1.95–2.15 (m, 4H), 3.07 (s, 3H), 3.31 (s, 3H), 3.6–3.85 (m, 4H), 4.58 (s, 2H), 6.8–7.3 (m, 5H).

The di-(4-methyl-3-oxo-2,3-dihydro-4H-1,4-benzoxazin-7-yl) disulphide used as a starting material was obtained as follows:

A mixture of 5-fluoro-2-nitrophenol (10.05 g), potassium carbonate (10.6 g) and acetone (125 ml) was heated to reflux for 10 minutes. The mixture was cooled to ambient temperature and a solution of ethyl bromoacetate (7.8 ml) in acetone (10 ml) was added dropwise. The mixture was heated to reflux for 2.5 hours. The mixture was evaporated and the residue was partitioned between diethyl ether and water. The organic phase was washed with water, dried (MgSO$_4$) and evaporated. There was thus obtained ethyl 2-(5-fluoro-2-nitrophenoxy)acetate (14.28 g, 92%), m.p. 44°–46° C.

A mixture of ethyl 2-(5-fluoro-2-nitrophenoxy)acetate (11 g), benzylmercaptan (5.2 g), triethylamine (5.08 g) and DMF (50 ml) was stirred and heated to 80° C. for 7 hours. The mixture was cooled, poured into water and acidified by the addition of dilute aqueous hydrochloric acid. The mixture was extracted with diethyl ether. The organic phase was washed with water and with brine, dried (MgSO$_4$) and evaporated to give ethyl 2-(5-benzylthio-2-nitrophenoxy)acetate (10.6 g, 68%) as a solid.

A mixture of a portion (8.68 g) of the product so obtained, stannous chloride dihydrate (*Tet. Lett.*, 1984, 839; 28.1 g), ethyl acetate (5 ml) and ethanol (50 ml) was heated to reflux for 30 minutes. The mixture was poured onto ice and a saturated aqueous sodium bicarbonate solution was added. The resultant precipitate was removed by filtration and the filtrate was extracted with ethyl acetate. The organic phase was washed with water and with brine, dried (MgSO$_4$) and evaporated to give 7-benzylthio-3-oxo-2,3-dihydro-4H-1,4-benzoxazine (3.32 g, 49%), m.p. 153°–154° C.

A portion (2.7 g) of the product so obtained was added to a stirred suspension of sodium hydride (60% w/w dispersion in mineral oil, 0.52 g; the oil was removed by washing the solid dispersion with petroleum ether) in DMF (10 ml) and the mixture was stirred at ambient temperature for 30 minutes. Methyl iodide (2.13 g) was added and the mixture was stirred at ambient temperature for 30 minutes. The mixture was partitioned between diethyl ether and water. The organic phase was washed with water and with brine, dried (MgSO$_4$) and evaporated to give 7-benzylthio-4-methyl-3-oxo-2,3-dihydro-4H-1,4-benzoxazine (2.6 g, 91%) as a solid.

A solution of 3-chloroperbenzoic acid (1.72 g) in chloroform (10 ml) was added dropwise to a solution of a portion (2 g) of the benzoxazine so obtained in chloroform (15 ml) which had been cooled to 0° C. and the mixture was stirred at 0° C. for 4 hours. Calcium hydroxide (0.74 g) was added and the mixture was stirred at ambient temperature for 15 minutes. The mixture was filtered and the filtrate was evaporated to give 7-benzylsulphinyl-4-methyl-3-oxo-2,3-dihydro-4H- 1,4-benzoxazine (2.1 g) as a solid which was used without further purification.

Trifluoroacetic acid (4.2 g) was added dropwise to a stirred suspension of a portion (1.5 g) of the benzoxazine so obtained in methylene chloride (45 ml) and the solution so obtained was stirred at ambient temperature for 30 minutes and then heated to reflux for 30 minutes. The mixture was evaporated and the residue was partitioned between ethyl acetate and water. The organic phase was washed with water and with a saturated aqueous sodium bicarbonate solution, dried (MgSO$_4$) and evaporated. The residue was purified by column chromatography using increasingly polar mixtures of methylene chloride and diethyl ether as eluent. There was thus obtained di-(4-methyl-3 -oxo-2,3-dihydro-4H-1,4-benzoxazin-7-yl) disulphide (0.68 g, 60%), m.p. 133°–135° C.

EXAMPLE 11

Using the procedure described in Example 5, (2S,4R)-4-( 5-bromothien-2-yl)-4-methoxy-2-methyltetrahydropyran was reacted with di-(4-tert-butylphenyl) disulphide to give (2S,4R)-4-[5-(4-tert-butylphenylthio)thien- 2-yl]-4-methoxy-2-methyltetrahydropyran in 38% yield as an oil.

NMR Spectrum (CD$_3$COCD$_3$, δ values) 1.20 (d, 3H), 1.3 (s, 9H), 1.3–2.3 (m, 4H), 3.1 (s, 3H), 3.6–3.9 (m, 3H), 7.0–7.5 (m, 6H).

The (2S,4R)-4-(5-bromothien-2-yl)-4-methoxy-2-methyltetrahydropyran used as a starting material was obtained as follows:

A solution of a mixture of 2,5-dibromothiophene (1.9 g) and ethyl bromide (2.56 g) in THF (6 ml) was added dropwise to a stirred suspension of magnesium (0.29 g) in diethyl ether (3 ml) and the mixture was warmed gently to promote the formation of a Grignard Reagent. The mixture was heated to 40° C. for 1 hour. The mixture was cooled in an ice-bath and a solution of (2S)-2-methyltetrahydropyran-4-one [European Patent Application No. 0385662 (Example 20 thereof); 0.61 g] in THF (5 ml) was added dropwise. The mixture was allowed to warm to ambient temperature and was stirred for 16 hours. The mixture was poured into a saturated aqueous ammonium chloride solution and extracted with ethyl acetate. The organic phase was washed with water and with brine, dried (MgSO$_4$) and evaporated. The residue was purified by column chromatography using initially methylene chloride and then increasingly polar mixtures of methylene chloride and diethyl ether as eluent. There was thus obtained, as a less polar isomer, (2S,4R)-4-(5-bromothien-2-yl)-4-hydroxy-2-methyltetrahydropyran (0.248 g, 19%) as an oil, having the 2-methyl and 4-hydroxy groups in a trans-relationship.

The product so obtained was reacted with methyl iodide using a similar procedure to that described in Example 1.-There was thus obtained the required starting material in 82% yield as an oil.

EXAMPLE 12

Using the procedure described in Example 5, (2S,4R)-4-(5 -bromothien-2-yl)-4-methoxy-2-methyltetrahydropyran was reacted with di-(1-methyl-2-thioxo-1,2,3,4-tetrahydroquinolin-6-yl) disulphide to give (2S,4R)-4-methoxy-2-methyl-4-[5-(1-methyl-2-thioxo-1,2,3,4 -tetrahydroquinolin-6-ylthio)thien-2-yl]tetrahydropyran in 55% yield as an oil.

NMR Spectrum ($CD_3COCD_3$, δ values) 1.15 (d, 3H), 1.25–2.25 (m, 4H), 2.7–3.25 (m, 4H), 3.08 (s, 3H), 3.60–3.90 (m, 3H), 3.85 (s, 3H), 7.0–7.35 (m, 5H).

EXAMPLE 13

Using the procedure described in Example 1, 4-[5-(4 -alpha-tert-butyldimethylsilyloxybenzyl)phenylthio)thien-2-yl]-4-hydroxytetrahydropyran was reacted with methyl iodide to give 4-[5-(4-(alpha-tert-butyldimethylsilyloxybenzyl)phenylthio)thien-2-yl] -4-methoxytetrahydropyran in 66% yield as an oil.

A mixture of the product so obtained (0.58 g), tetrabutylammonium fluoride (0.1M in THF, 0.4 ml) and THF (1 ml) was stirred at ambient temperature of 16 hours. The mixture was evaporated and the residue was partitioned between ethyl acetate and water. The organic phase was washed with water, dried ($MgSO_4$) and evaporated. The residue was purified by column chromatography using a 47:3 v/v mixture of methylene chloride and diethyl ether as eluent. There was thus obtained 4-[5-(4-(alpha-hydroxybenzyl)phenylthio)thien- 2-yl]-4-methoxytetrahydropyran (0.041 g, 91%), m.p. 109°–110° C.

The 4-[5-(4-(alpha-tert-butyldimethylsilyloxybenzyl)phenylthio)thien- 2-yl]-4-hydroxytetrahydropyran used as a starting material was obtained as follows:

A mixture of the copper (I) salt of 4-bromophenylthiol [2.51 g; obtained by heating a mixture of cuprous oxide (1.86 g), 4-bromophenylthiol (5 g) and ethanol (30 ml) to reflux for 3 hours and filtration], 2-bromothiophene (1.2 ml), pyridine (0.5 ml) and quinoline (8 ml) was heated to 200° C. for 3 hours. The mixture was cooled to ambient temperature and partitioned between 6N aqueous hydrochloric acid and diethyl ether. The organic phase was dried ($MgSO_4$) and evaporated. The residue was purified by column chromatography using a 19:1 v/v mixture of petroleum ether (b.p. 40°–60° C.) and methylene chloride as eluent. There was thus obtained 4-bromophenyl 2-thienyl sulphide (0.926 g, 34%), as an oil.

A Grignard reagent was prepared from 4-bromophenyl 2-thienyl sulphide (1.2 g) by the dropwise addition of a solution of the material in THF (2 ml) to a suspension of magnesium (0.09 g) in THF (2.5 ml) which was warmed gently to aid the initiation of the reaction. Care was required to ensure initiation of the reaction before the bulk of the 4-bromophenyl 2-thienyl sulphide had been added, otherwise a vigorous exothermic reaction could occur. After the completion of the addition the mixture was stirred at ambient temperature until all of the magnesium had been consumed. Benzaldehyde (0.38 ml) was added dropwise and the mixture was stirred at ambient temperature for 16 hours. The mixture was poured onto a mixture of ice and aqueous ammonium chloride solution (15% w/v) and extracted with ethyl acetate. The organic phase was washed with water, dried ($MgSO_4$) and evaporated. The residue was purified by column chromatography using a 10:1 v/v mixture of petroleum ether (b.p. 40°–60° C.) and diethyl ether as eluent. There was thus obtained 4-(alpha-hydroxybenzyl)phenyl 2-thienyl sulphide (0.25 g, 23%), as an oil.

After repetition of the above-mentioned steps, a mixture of the product so obtained (0.413 g), tert-butyldimethylsilyl chloride (0.521 g), imidazole (0.472 g) and DMF (1.5 ml) was stirred at ambient temperature for 3 hours. The mixture was partitioned between diethyl ether and cold water, dried ($MgSO_4$) and evaporated. The residue was purified by column chromatography using petroleum ether (b.p. 40°–60° C.) as eluent. There was thus obtained 4-(alpha-tert-butyldimethylsilyloxybenzyl)phenyl 2-thienyl sulphide (0.227 g, 40%) as an oil.

n-Butyl-lithium (1.5M in hexane, 0.35 ml) was added dropwise to a solution of the product so obtained (0.225 g) in THF (2 ml) which had been cooled to −78° C. The mixture was stirred at −78° C. for 2 hours. Tetrahydropyran-4-one (0.06 g) was added to the mixture which was stirred for 16 hours and allowed to warm slowly to ambient temperature. The mixture was partitioned between a cold saturated aqueous ammonium chloride solution and ethyl acetate. The organic layer was washed with water, dried ($MgSO_4$) and evaporated. The residue was purified by column chromatography using a 9:1 v/v mixture of methylene chloride and diethyl ether as eluent. There was thus obtained the required starting material (0.09 g, 32%) m.p. 118°–120° C.

EXAMPLE 14 n-Butyl-lithium (1.6M in hexane, 2.6 ml) was added dropwise to a solution of 4-[5-(4-bromophenylthio)thien-2-yl]-4-methoxytetrahydropyran (1.58 g) in THF (16 ml) which had been cooled to −110° C. The mixture was stirred at −110° C. for 2 hours. 4-Fluorobenzaldehyde (0.44 ml) was added dropwise. The mixture was stirred and allowed to warm slowly to ambient temperature. The mixture was poured into a saturated aqueous ammonium chloride solution and extracted with ethyl acetate. The organic phase was washed with water, dried ($MgSO_4$) and evaporated. The residue was purified by column chromatography using a 2:3 v/v mixture of petroleum ether (b.p. 40°–60° C.) and diethyl ether as eluent. There was thus obtained 4-[5-(4-(4-fluoro-alpha-hydroxybenzyl)phenylthio)thien-2-yl]-4-methoxytetrahydropyran (1.29 g, 73%), as an oil.

NMR Spectrum ($CD_3COCD_3$, δ values) 1.85–2.15 (m, 4H), 3.05 (s, 3H), 3.6–3.8 (m, 4H), 4.9 (s, 1H), 5.85 (s,1H), 6.75–7.5 (m, 10H).

EXAMPLE 15

The procedure described in Example 14 was repeated except that 2,4-difluorobenzaldehyde was used in place of 4-fluorobenzaldehyde. There was thus obtained 4-[5-(4-(2, 4-difluoroalpha-hydroxybenzyl)phenylthio)thien- 2-yl]-4-methoxytetrahydropyran in 33% yield as an oil.

NMR Spectrum ($CD_3COCD_3$, δ values) 1.85–2.15 (m, 4H), 3.05 (s, 3H), 3.6–3.8 (m, 4H), 6.7–7.5 (m, 9H).

EXAMPLE 16

The procedure described in Example 14 was repeated except that pentafluorobenzaldehyde was used in place of 4-fluorobenzaldehyde. The was thus obtained 4-[5-(4-(2,3, 4,5,6 -pentafluoro-alpha-hydroxybenzyl)phenylthio)thien-2-yl]-4 -methoxytetrahydropyran in 49% yield as an oil.

NMR Spectrum (CD$_3$COCD$_3$, δ values) 1.8–2.15 (m, 4H), 3.05 (s, 3H), 3.6–3.8 (m, 4H), 6.25 (s, 1H), 7.0–7.5 (m, 6H).

EXAMPLE 17

The procedure described in Example 14 was repeated except that 4-trifluoromethylbenzaldehyde was used in place of 4-fluorobenzaldehyde. There was thus obtained 4-[5-(4-(alpha-hydroxy- 4-trifluoromethylbenzyl)phenylthio)thien-2-yl]-4-methoxytetrahydropyran in 79% yield as an oil.

NMR Spectrum (CD$_3$COCD$_3$, δ values) 1.8–2.1 (m, 4H), 3.05 (s, 3H), 3.5–3.75 (m, 4H), 5.05 (d, 1H), 5.8 (d, 1H), 7.0–7.75 (m, 10H).

EXAMPLE 18

Pyridinium chlorochromate (1.19 g) was added portionwise to a stirred solution of 4-[5-(4-(4-fluoro-alpha-hydroxybenzyl)phenylthio)thien- 2-yl]-4-methoxytetrahydropyran (0.95 g) in methylene chloride (20 ml) and the mixture was stirred at ambient temperature for 12 hours. The mixture was filtered and the filtrate was evaporated. The residue was purified by column chromatography using a 3:2 v/v mixture of petroleum ether (b.p. 40°–60° C.) and diethyl ether as eluent. There was thus obtained 4-(5-(4-(4-fluorobenzoyl)phenylthio)thien- 2-yl]-4-methoxytetrahydropyran (0.683 g, 72%), m.p. 81° C.

EXAMPLE 19

Using the procedure described in Example 18, 4-[5-(4-(2,4 -difluoro-alpha-hydroxybenzyl)phenylthio)thien-2-yl]-4-methoxytetrahydropyran was reacted with pyridinium chlorochromate to give 4-[5-(4-(2,4-difluorobenzoyl)phenylthio)thien-2-yl]-4-methoxytetrahydropyran in 71% yield, as an oil.

NMR Spectrum (CD$_3$COCD$_3$, δ values) 1.9–2.15 (m, 4H), 3.1 (s, 3H), 3.6–3.8 (m, 4H), 7.0–7.8 (m, 9H).

EXAMPLE 20

Using the procedure described in Example 18, 4-[5-(4-(2,3,4,5,6-pentafluoro-alpha-hydroxybenzyl)phenylthio)thien-2-yl]-4-methoxytetrahydropyran was reacted with pyridinium chlorochromate to give 4-[5-(4-(2,3,4,5,6-pentafluorobenzoyl)phenylthio)thien-2-yl]-4-methoxytetrahydropyran in 75% yield, m.p. 93°–94° C.

EXAMPLE 21

Using the procedure described in Example 18, 4-[5-(4-(alphahydroxy- 4-trifluoromethylbenzyl)phenylthio)thien-2-yl]-4-methoxytetrahydropyran was reacted with pyridinium chlorochromate to give 4-[5-(4-(4-trifluoromethylbenzoyl)phenylthio)thien-2-yl]-4-methoxytetrahydropyran in 75% yield, m.p. 86°–87° C.

EXAMPLE 22

Lithium di-isopropylamide was prepared by the addition of n-butyl-lithium (1.6M in hexane, 2.44 ml) to a solution of di-isopropylamine (0.394 g) in THF (5 ml) which had been cooled to −78° C. The mixture was stirred at −78° C. for 15 minutes and then cooled to −85° C. A solution of 4-(5-bromothien-2-yl)-4-methoxytetrahydropyran (1 g) in THF (15 ml) was added dropwise and the mixture was stirred at −85° C. for 2 hours. A solution of di-(1-methyl-2-oxo-1,2,3,4-tetrahydroquinolin-6-yl) disulphide (1.5 g) in THF (3 ml) was added dropwise and the mixture was stirred for 4 hours and allowed to warm to ambient temperature. The mixture was partitioned between a saturated aqueous ammonium chloride solution and ethyl acetate. The organic phase was washed with water, dried (MgSO$_4$) and evaporated. The residue was purified by column chromatography using diethyl ether as eluent. There was thus obtained 4-[4-bromo-5-(1-methyl-2-oxo- 1,2,3,4-tetrahydroquinolin-6-ylthio)thien-2-yl]-4-methoxytetrahydropyran (0.43 g, 26%), as a foam.

NMR Spectrum (CD$_3$COCD$_3$, δ values) 1.9–2.2 (m, 4H), 2.5–3.05 (m, 4H), 3.1 (s, 3H), 3.3 (s, 3H), 3.65–3.7 (m, 4H), 7.0–7.35 (m, 4H).

EXAMPLE 23

Using the procedure described in Example 5, (2RS,4SR)-4-(5-bromothien-2-yl)-4-methoxy-2-methyltetrahydropyran was reacted with di-(4-tert-butylphenyl) disulphide to give (2RS,4SR)-4-[5-(4-tert-butylphenylthio)thien-2-yl]-4-methoxy-2-methyltetrahydropyran in 77% yield as an oil.

NMR Spectrum (CD$_3$COCD$_3$, δ values) 1.20 (d, 3H), 1.3 (s, 9H), 1.3–2.3 (m, 4H), 3.1 (s, 3H), 3.6–3.9 (m, 3H), 7.0–7.5 (m, 6H).

The (2RS,4SR)-4-(5-bromothien-2-yl)-4-methoxy-2-methyltetrahydropyran, used as a starting material, was obtained as follows:

The procedure described in the portion of Example 11 which is concerned with the preparation of starting materials was repeated except that (2RS)-2-methyltetrahydropyran-4-one (*J. Amer. Chem. Soc.*, 1982, 104, 4666) was used in place of (2S)-2-methyltetrahydropyran- 4-one. There was thus obtained, as a less polar isomer, (2RS,4SR)-4-(5-bromothien-2-yl)-4-hydroxy-2-methyltetrahydropyran in 20% yield as an oil.

The product so obtained was reacted with methyl iodide using a similar procedure to that described in Example 1. There was thus obtained the required starting material in 74% yield as an oil.

EXAMPLE 24

Using the procedure described in Example 5, (2RS,4SR)-4-(5-bromothien-2-yl)-4-methoxy-2-methyltetrahydropyran was reacted with di-(1-methyl-2-thioxo-1,2,3,4-tetrahydroquinolin-6-yl) disulphide to give (2RS,4SR)-4-methoxy-2-methyl-4-[5-(1-methyl-2-thioxo-1,2,3,4 -tetrahydroquinolin-6-ylthio)thien-2-yl]tetrahydropyran in 72% yield, as an oil.

NMR Spectrum (CD$_3$COCD$_3$, δ values) 1.15 (d, 3H), 1.25–2.25 (m, 4H), 2.7–3.25 (m, 4H), 3.08 (s, 3H), 3.60–3.90 (m, 3H), 3.85 (s, 3H), 7.0–7.35 (m, 5H).

EXAMPLE 25

Using the procedure described in Example 6, 4-methoxy-4-(3-thienyl)tetrahydropyran was reacted with di-(1-methyl-2-oxo-1,2,3,4-tetrahydroquinolin-6-yl) disulphide to give 4-methoxy-4-[2-(1-methyl-2-oxo-1,2,3,4-tetrahydroquinolin-6-ylthio)thien- 4-yl]- tetrahydropyran in 26% yield, m.p. 106°–108° C.

EXAMPLE 26

The following illustrate representative pharmaceutical dosage forms containing the compound of formula I, or a pharmaceutically-acceptable salt thereof (hereafter compound X), for therapeutic or prophylactic use in humans:

| (a) Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |
| (b) Tablet II | |
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |
| (c) Tablet III | |
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |
| (d) Capsule | mg/capsule |
| Compound X | 10 |
| Lactose Ph.Eur | 488.5 |
| Magnesium stearate | 1.5 |
| (e) Injection I | (50 mg/ml) |
| Compound X | 5.0% w/v |
| 1M Sodium hydroxide solution | 15.0% v/v |
| 0.1M Hydrochloric acid (to adjust pH to 7.6) | |
| Polyethylene glycol 400 | 4.5% w/v |
| Water for injection to 100% | |
| (f) Injection II | (10 mg/ml) |
| Compound X | 1.0% w/v |
| Sodium phosphate BP | 3.6% w/v |
| 0.1M Sodium hydroxide solution | 15.0% v/v |
| Water for injection to 100% | |
| (g) Injection III | (1 mg/ml, buffered to pH6) |
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |
| (h) Aerosol I | mg/ml |
| Compound X | 10.0 |
| Sorbitan trioleate | 13.5 |
| Trichlorofluoromethane | 910.0 |
| Dichlorodifluoromethane | 490.0 |
| (i) Aerosol II | |
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |
| (j) Aerosol III | |
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |
| (k) Aerosol IV | |
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

Note

The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

CHEMICAL FORMULAE

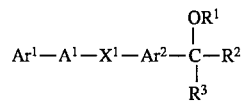

I

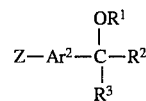

II

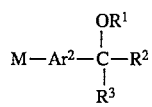

III

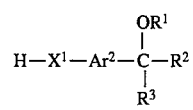

IV

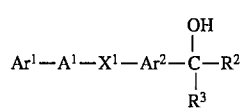

V

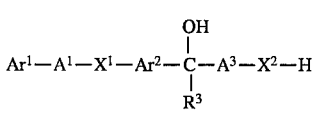

VI

SCHEME I

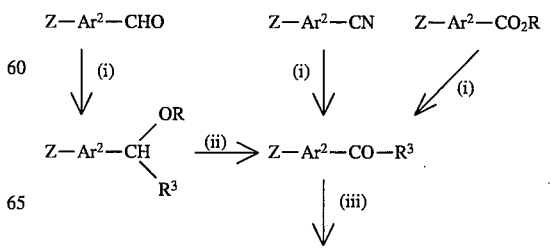

SCHEME I (continued)
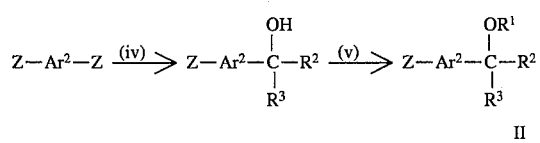
Reagents
- (i) R³Li or R³MgZ, THF
- (ii) DDQ or MnO₂
- (iii) R²Li or R²MgZ, THF;
- (iv) BuLi or Mg, THF; R²COR³, THF
- (v) R¹Z, base
Note  R = (1–4C)alkyl such as Me or Et
SCHEME II
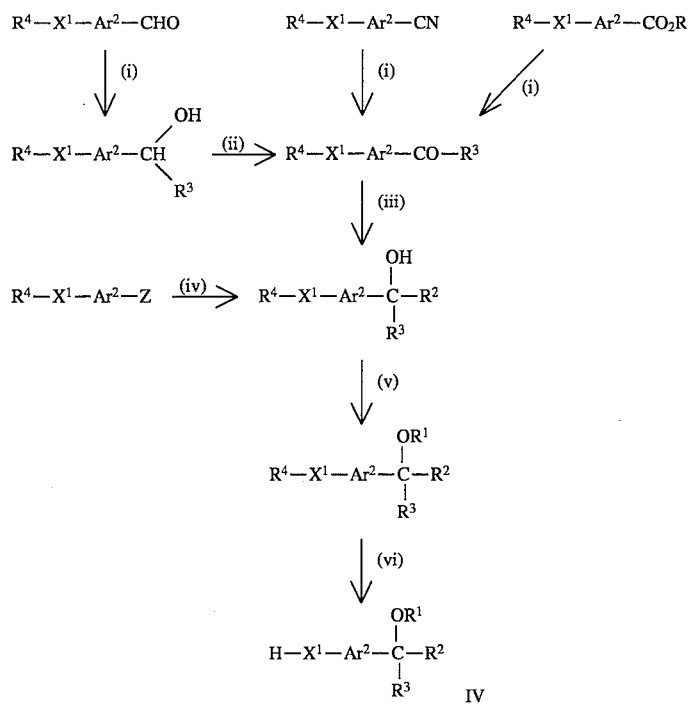
Reagents
- (i) to (v) as in Scheme I
- (vi) Conventional removal of the protecting group R⁴ which is, e.g., COMe, THP, CH₂Ph or Me.
SCHEME III
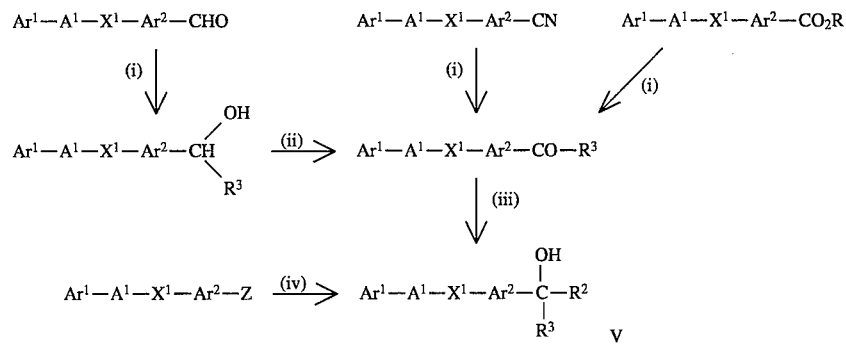

-continued
SCHEME III

Reagents (i) to (iv)   as in Scheme I

SCHEME IV

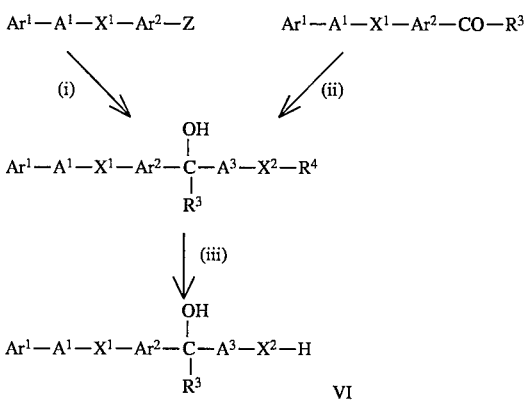

Reagents (i)   BuLi or Mg, THF; $R^3$—CO—$A^3$—$X^2$—$R^4$
(ii)  $R^4$—$X^2$—$A^3$—Li or $R^4$—$X^2$—$A^3$—MgZ, THF
(iii) Conventional removal of the protecting group $R^4$ which is, e.g. COMe, THP, $CH_2Ph$ or Me.

What I claim is:

1. A heterocyclene compound of the formula I

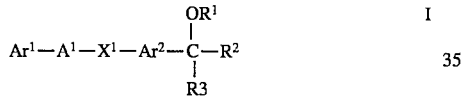

wherein $Ar^1$ is phenyl or naphthyl optionally having up to five substituents selected from amino, halogeno, hydroxy, cyano, oxo, thioxo, (1–4C) alkyl, (1–4C) alkoxy, (1–4C) alkylthio, (1–4C) alkylsulphinyl, (1–4C) alkylsulphonyl, (1–4C) alkylamino, di-[(1–4C)alkyl]amino, (2–4C)alkanoyl, fluoro-(1–4C)alkyl, cyano-(1–4C)alkyl, phenyl, benzoyl and phenyl-(1–4C)alkyl, and wherein said phenyl, benzoyl or phenyl-(1–4C)alkyl substituent optionally has a substituent selected from halogeno, (1–4C)alkyl and (1–4C)alkoxy;

wherein $A^1$ is a direct link to $X^1$ or is (1–3C)alkylene;

wherein $X^1$ is oxy, thio, sulphinyl, sulphonyl or imino;

$Ar^2$ is a 5-membered heterocyclene moiety having one heteroatom selected from nitrogen, oxygen and sulphur, optionally having one substituent selected from halogeno, (1–4C)alkyl and (1–4C)alkoxy;

wherein $R^1$ is (1–4C)alkyl, (3–4C)alkenyl or (3–4C)alkynyl; and wherein $R^2$ and $R^3$ together form a group of the formula —$A^2$—$X^2$—$A^3$— which, together with the carbon atom to which $A^2$ and $A^3$ are attached, defines a ring having 5 to 7 ring atoms, wherein $A^2$ and $A^3$, which are the same or different, each is (1–3C)alkylene and $X^2$ is oxy, thio, sulphinyl or sulphonyl, and which ring optionally has one, two or three substituents, which are the same or different, selected from hydroxy, (1–4C)alkyl and (1–4C) alkoxy;

or a pharmaceutically-acceptable salt thereof.

2. A heterocyclene compound of the formula I

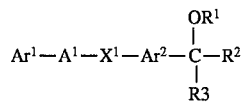

wherein $Ar^1$ is phenyl or naphthyl optionally having up to five substituents selected from amino, halogeno, hydroxy, cyano, oxo, thioxo, (1–4C) alkyl, (1–4C) alkoxy, (1–4C) alkylthio, (1–4C)alkylsulphinyl, (1–4C)alkylsulphonyl, (1–4C)alkylamino, di-[(1–4C)alkyl]amino, (2–4C)alkanoyl, fluoro-(1–4C)alkyl, cyano-(1–4C)alkyl, phenyl, benzoyl, phenyl-(1–4C)alkyl, α,α-difluorobenzyl, α-hydroxybenzyl and α-[(1–4C) alkoxy]benzyl, and wherein said six last-mentioned substituents may optionally have a substituent selected from halogeno, (1–4C)alkyl and (1–4C) alkoxy;

wherein $A^1$ is a direct link to $X^1$ or is (1–3C)alkylene;

wherein $X^1$ is oxy, thio, sulphinyl, sulphonyl or imino;

$Ar^2$ is a 5-membered heterocyclene moiety having one heteroatom selected from nitrogen, oxygen and sulphur, optionally having one substituent selected from halogeno, (1–4C) alkyl and (1–4C) alkoxy;

wherein $R^1$ is (1–4C)alkyl, (3–4C)alkenyl or (3–4C)alkynyl; and wherein $R^2$ and $R^3$ together form a group of the formula —$A^2$—$X^2$—$A^3$— which, together with the carbon atom to which $A^2$ and $A^3$ are attached, defines a ring having 5 to 7 ring atoms, wherein $A^2$ and $A^3$, which are the same or different, each is (1–3C)alkylene and $X^2$ is oxy, thio, sulphinyl or sulphonyl, and which ring optionally has one, two or three substituents, which are the same or different, selected from hydroxy, (1–4C)alkyl and (1–4C) alkoxy;

or a pharmaceutically-acceptable salt thereof.

3. A heterocyclene compound of the formula I

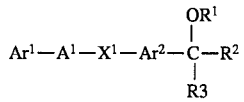

wherein $Ar^1$ is phenyl or naphthyl optionally having up to five substituents selected from amino, halogeno, hydroxy, cyano, oxo, thioxo, (1–4C) alkyl, (1–4C) alkoxy, (1–4C) alkylthio, (1–4C) alkylsulphinyl, (1–4C) alkylsulphonyl, (1–4C) alkylamino, di-[(1–4C)alkyl]amino, (2–4C)alkanoyl, fluoro-(1–4C)alkyl, cyano-(1–4C) alkyl, phenyl, benzoyl, phenyl-(1–4C) alkyl, α,α-difluorobenzyl, α-hydroxybenzyl and α-[(1–4C) alkoxy]benzyl, and wherein said six last-mentioned substituents optionally have up to five substituents selected from halogeno, trifluoromethyl, (1–4C)alkyl and (1–4C)alkoxy;

wherein $A^1$ is a direct link to $X^1$ or is (1–3C)alkylene;

wherein $X^1$ is oxy, thio, sulphinyl, sulphonyl or imino;

$Ar^2$ is a 5-membered heterocyclene moiety having one heteroatom selected from nitrogen, oxygen and sulphur, optionally having one substituent selected from halogeno, (1–4C)alkyl and (1–4C) alkoxy;

wherein $R^1$ is (1–4C)alkyl, (3–4C)alkenyl or (3–4C)alkynyl; and wherein $R^2$ and $R^3$ together form a group of the formula —$A^2$—$X^2$—$A^3$— which, together with the carbon atom to which $A^2$ and $A^3$ are attached, defines a ring having 5 to 7 ring atoms, wherein $A^2$ and $A^3$, which are the same or different, each is (1–3C)alkylene and $X^2$ is oxy, thio, sulphinyl or sulphonyl, and which ring optionally has one, two or three substituents, which are the same or different, selected from hydroxy, (1–4C)alkyl and (1–4C)alkoxy;

or a pharmaceutically-acceptable salt thereof.

4. A heterocyclene compound of the formula I as claimed in claim 1 wherein $Ar^1$ is 4-tert-butylphenyl or naphth-2-yl;

$A^1$ is a direct link to $X^1$;

$X^1$ is thio;

$Ar^2$ is 2,5-thienylene;

$R^1$ is methyl; and $R^2$ and $R^3$ together form a group of the formula —$A^2$—$X^2$—$A^3$— which, together with the carbon atom to which $A^2$ and $A^3$ are attached, defines a ring having 5 or 6 ring atoms, wherein $A^2$ is ethylene, $A^3$ is methylene or ethylene and $X^2$ is oxy, and which ring optionally has a methyl substituent alpha to $X^2$;

or a pharmaceutically-acceptable salt thereof.

5. A pharmaceutical composition which comprises a heterocyclene compound of the formula I, or a pharmaceutically-acceptable salt thereof, as claimed in any one of claims 1 to 4 in association with a pharmaceutically-acceptable diluent or carrier.

6. A method of treating a disease or medical condition mediated alone or in part by one or more leukotrienes which comprises administering to a warm-blooded animal requiring such treatment an effective amount of a heterocyclene compound of the formula I, or a pharmaceutically-acceptable salt thereof, as claimed in any one of claims 1 to 4.

* * * * *